United States Patent
Takahara et al.

(10) Patent No.: US 11,773,374 B2
(45) Date of Patent: Oct. 3, 2023

(54) METHOD FOR PRODUCING PURIFIED PLATELETS, METHOD FOR PRODUCING PLATELET PRODUCT, METHOD FOR PRODUCING BLOOD PRODUCT, PLATELET PRESERVING SOLUTION, PLATELET PRESERVING AGENT, AND METHOD FOR PRESERVING PLATELETS

(71) Applicant: MEGAKARYON CORPORATION, Kyoto (JP)

(72) Inventors: Hiroya Takahara, Kyoto (JP); Junko Tomizuka, Kyoto (JP); Haruki Okamoto, Kyoto (JP); Hidenori Hirose, Kyoto (JP)

(73) Assignee: MEGAKARYON CORPORATION, Kyoto (JP)

( * ) Notice: Subject to any disclaimer, the term of this patent is extended or adjusted under 35 U.S.C. 154(b) by 698 days.

(21) Appl. No.: 16/648,551

(22) PCT Filed: Sep. 19, 2018

(86) PCT No.: PCT/JP2018/034667
§ 371 (c)(1),
(2) Date: Mar. 18, 2020

(87) PCT Pub. No.: WO2019/059235
PCT Pub. Date: Mar. 28, 2019

(65) Prior Publication Data
US 2020/0216809 A1    Jul. 9, 2020

(30) Foreign Application Priority Data
Sep. 19, 2017  (JP) .................................. 2017-179138

(51) Int. Cl.
| | |
|---|---|
| *C12N 5/078* | (2010.01) |
| *B01D 21/26* | (2006.01) |
| *B04B 15/12* | (2006.01) |
| *B01D 63/02* | (2006.01) |

(52) U.S. Cl.
CPC ......... *C12N 5/0644* (2013.01); *B01D 21/262* (2013.01); *B04B 15/12* (2013.01); *B01D 63/02* (2013.01)

(58) Field of Classification Search
CPC ............ C12N 5/0644; C12N 2501/165; C12N 2501/606; C12N 2506/45; C12N 2510/04; B01D 21/262; B01D 63/02; B01D 2311/04; B01D 2311/2688; B01D 2313/48; B01D 61/18; B01D 65/02; B01D 2313/50; B01D 2321/16; B04B 15/12; A61M 1/0272; A61M 2202/0427; A01N 1/0242; A01N 1/0221; A61K 35/19; A61P 7/04
USPC .................................................. 494/43, 37
See application file for complete search history.

(56) References Cited

U.S. PATENT DOCUMENTS

| | | | | |
|---|---|---|---|---|
| 5,364,526 | A * | 11/1994 | Matkovich | A61M 1/0209 210/206 |
| 7,858,296 | B2 * | 12/2010 | Sowemimo-Coker | C12N 5/0634 435/2 |
| 2014/0271590 | A1 * | 9/2014 | Feng | C12N 5/0644 435/325 |
| 2015/0056602 | A1 * | 2/2015 | Radwanski | A61M 1/3693 494/37 |
| 2016/0272941 | A1 * | 9/2016 | Baruch | G01N 15/1056 |
| 2018/0171278 | A1 | 6/2018 | Kiyama et al. | |
| 2018/0282697 | A1 * | 10/2018 | Hirose | C12N 5/0644 |

FOREIGN PATENT DOCUMENTS

| | | |
|---|---|---|
| EP | 0 664 159 | 7/1995 |
| EP | 0 813 361 | 11/2003 |
| EP | 0 910 622 | 9/2012 |
| EP | 2 500 418 | 9/2012 |
| EP | 2 708 597 | 3/2014 |
| EP | 2 955 223 | 12/2015 |
| EP | 3 351 627 | 7/2018 |
| EP | 3 363 443 | 8/2018 |
| EP | 3 372 674 | 9/2018 |
| EP | 3 594 325 | 1/2020 |
| EP | 3 650 535 | 5/2020 |

(Continued)

OTHER PUBLICATIONS

Office Action issued in corresponding Japanese Patent Application No. JP 2019-543675, dated Jun. 7, 2022, 18 pages w/translation.
"Platelet storage in 60% bicarbonated Ringer's solution/40% plasma", Transfusion Medicine, Official Journal of the British Blood Transfusion Society, Jul. 17, 2017, 28, 80-82.
Chapter 5 Human Albumin,Transfusion Medicine and Hemotherapy, 2009, 36, 399-407.
Oikawa, et al., "Storage of washed platelets in BRS—A platelet additive solutions based on two types of clinically available bicarbonated Ringer's solutions with different electrolyte concentrations", Transfusion and Apheresis Science, 53, 2015, 233-237 http://dx.doi.org/10.1016/j.transci.2015. 05. 002.

(Continued)

*Primary Examiner* — Walter D. Griffin
*Assistant Examiner* — Shuyi S. Liu
(74) *Attorney, Agent, or Firm* — Hamre, Schumann, Mueller & Larson, P.C.

(57) ABSTRACT

Provided is a method for producing platelets, in which damage to platelets is suppressed compared with a method in which platelets are separated using a filter from a megakaryocyte culture, and then the platelets are concentrated using a hollow fiber membrane and are further washed using the hollow fiber membrane, and purified platelets can be produced in a shorter period of time compared with the time that is taken to perform the above-described method so as to reduce damage to platelets. The method for producing purified platelets of the present invention includes a concentrating step of concentrating a megakaryocyte culture, and a centrifuging step of centrifuging platelets from an obtained concentrate.

4 Claims, 1 Drawing Sheet

(56) References Cited

FOREIGN PATENT DOCUMENTS

| | | | | |
|---|---|---|---|---|
| JP | 7-284529 | 10/1995 | | |
| JP | 10-511402 | 11/1998 | | |
| JP | 2000-506024 | 5/2000 | | |
| JP | 2001-194370 | 7/2001 | | |
| JP | 2005-296675 | 10/2005 | | |
| JP | 2016-116465 | 6/2016 | | |
| JP | 2016-220590 | 12/2016 | | |
| JP | 2016-538859 | 12/2016 | | |
| WO | 2011/034073 | 3/2011 | | |
| WO | 2012/157586 | 11/2012 | | |
| WO | 2014/123242 | 8/2014 | | |
| WO | 2017/065280 | 4/2017 | | |
| WO | WO-2017065280 A1 * | 4/2017 | ............. | A61K 35/14 |

OTHER PUBLICATIONS

Robert, et al., "Megakaryocyte and Platelet Production from Human Cord Blood Stem Cells", Platelets and Megakaryocytes: vol. 3, Additional Protocols and Perspectives, Methods in Molecular Biology, 2012, vol. 788, pp. 219-247, DOI10.1007/978-1-61779-307-3_16.

Takayama et al., "Generation of functional platelets from human embryonic stem cells in vitro via ES-sacs, VEGF-promoted structures that concentrate hematopoietic progenitors", Blood, vol. 111, No. 11, pp. 5298-5306 (2008).

Nakamura et al., "Expandable Megakaryocyte Cell Lines Enable Clinically Applicable Generation of Platelets from Human Induced Pluripotent Stem Cells", Cell Stem Cell, vol. 14, No. 4, pp. 535-548 (2014).

Oguro et al., "Senescence and ageing of stem cells regulated by polycomb complexes", Regenerative Medicine, vol. 6, No. 4, pp. 26-32 (2007)—Abstract.

Gil et al., "Regulation of the INK4b-ARF-INK4a tumour suppressor locus: all for one or one for all", Nature Reviews Molecular Cell Biology, vol. 7, pp. 667-677 (2006)—Abstract only.

Kim et al., "Absence of p16INK4a and truncation of ARF tumor suppressors in chickens", PNAS, vol. 100, No. 1, pp. 211-216 (2003).

Takayama et al., "Transient activation of c-MYC expression is critical for efficient platelet generation from human induced pluripotent stem cells", J. Exp. Med., vol. 207, No. 13, pp. 2817-2830 (2010).

Kobayashi et al., "Generation of Rat Pancreas in Mouse by Interspecific Blastocyst Injection of Pluripotent Stem Cells", Cell, vol. 142, No. 5, pp. 787-799 (2010).

Okada et al., "Significance of Albumin in Artificial Preservative Solution of platelet", Blood Programme, The abstract of the 12th Society for Japanese Blood Programme, General Topic 149, p. 109 (1988)—partial translation.

Shigemori et al., "Development of in vitro-produced platelet products from induced pluripotent stem cells", Journal of clinical and experimental medicine, vol. 257, No. 3. pp. 208-212 (2016)—partial translation.

Schlinker et al., "Separation of In-Vitro-Derived Megakaryocytes and Platelets Using Spinning-Membrane Filtration", Biotechnology and Bioengineering, vol. 112, No. 4, pp. 788-800 (2015).

International Search Report issued in International Application No. PCT/JP2018/034667, dated Dec. 25, 2018, 8 pages.

Extended European Search Report issued in corresponding European Patent Application No. 18858726.5, dated May 11, 2021, 8 pages.

Office Action issued in corresponding Japanese Patent Application No. 2019-543575, dated Jan. 6, 2023, 14 pages w/translation.

* cited by examiner

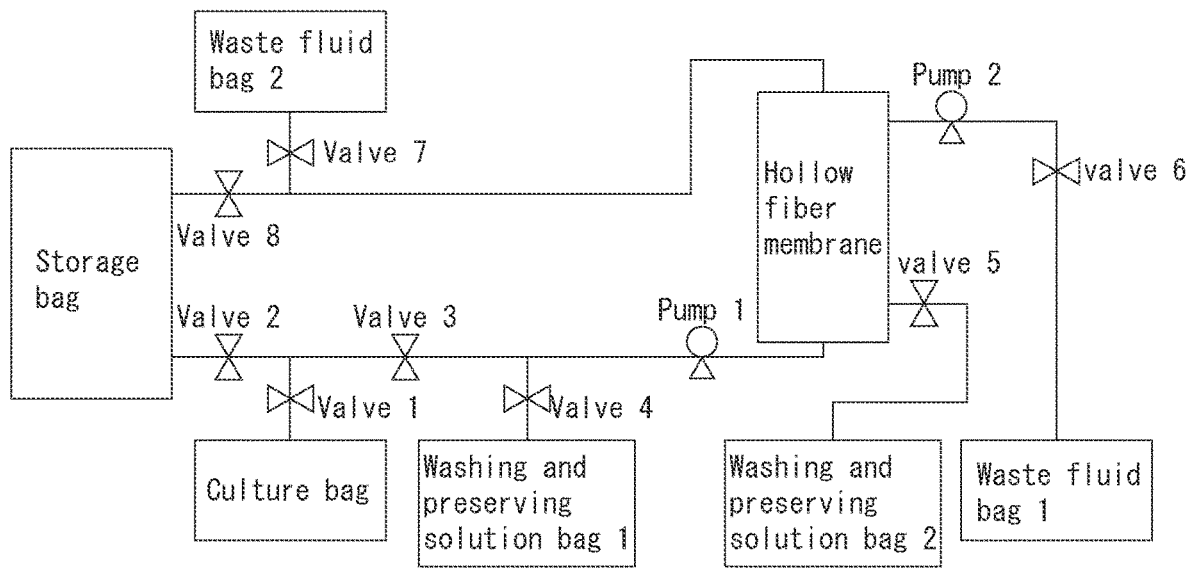

METHOD FOR PRODUCING PURIFIED PLATELETS, METHOD FOR PRODUCING PLATELET PRODUCT, METHOD FOR PRODUCING BLOOD PRODUCT, PLATELET PRESERVING SOLUTION, PLATELET PRESERVING AGENT, AND METHOD FOR PRESERVING PLATELETS

TECHNICAL FIELD

The present invention relates to a method for producing purified platelets, a method for producing a platelet product, a method for producing a blood product, a platelet preserving solution, a platelet preserving agent, and a method for preserving platelets.

BACKGROUND ART

Platelet products are administered to patients who are bleeding due to operations, injuries, or the like, or who are suffering from low levels of platelets, or the like. Currently, platelet products are produced from blood obtained through blood donation. However, due to a change in the population composition, there is a concern that the amount of blood donated will decrease and cause a shortage of platelet products.

Furthermore, if blood donors have infectious diseases involving bacteria or the like, their blood may be contaminated with bacteria, and thus there is a risk of infectious diseases caused by administration of platelet products contaminated with bacteria. Thus, methods for producing platelets in vitro are developed (Non-Patent Literature 1). When producing platelet products from produced platelets, platelets are purified from a culture, and are filled into blood bags or the like.

CITATION LIST

Non-Patent Literature

Non-Patent Literature 1: Takayama N et.al, "Generation of functional platelets from human embryonic stem cells in vitro via ES-sacs, VEGF-promoted structures that concentrate hematopoietic progenitors.", 2008, Blood, Vol. 111, No. 11, pages 5298-5306

SUMMARY OF INVENTION

Technical Problem

As a method for purifying platelets from a megakaryocyte culture, a method is conceivable in which platelets are separated using a filter from a megakaryocyte culture, and then the platelets are concentrated using a hollow fiber membrane and are further washed using the hollow fiber membrane (hereinafter, alternatively referred to as the "above-described method").

However, when producing one platelet product, it is necessary to separate and purify platelets from a large amount of megakaryocyte culture (e.g., 50 L of culture). Therefore, in order to produce a platelet product from a culture in a certain period of time, the flow rate during separation through filtering has to be increased. However, if the flow rate during separation through filtering is increased, the pressure that is applied to the culture when a filter or the like is clogged has to be increased. Therefore, the pressure that is applied to platelets in culture increases, and there is a problem in that the platelets are damaged (e.g., expression of Annexin V increases).

Thus, it is a first object of the present invention to provide a method for producing purified platelets, for example, in which damage to platelets is suppressed compared with the above-described method, and purified platelets can be produced in a shorter period of time compared with the time that is taken to perform the above-described method so as to reduce damage to platelets.

Furthermore, it is a second object of the present invention to provide a platelet preserving solution suited to preserve obtained purified platelets.

Solution to Problem

In order to achieve the first object, the present invention is directed to a method for producing purified platelets (hereinafter, alternatively referred to as a "method for producing platelets"), including: a concentrating step of concentrating a megakaryocyte culture; and a centrifuging step of centrifuging platelets from an obtained concentrate.

Also, the present invention is directed to a method for producing a platelet product, including a product producing step of producing a platelet product from purified platelets,
  wherein the purified platelets are obtained using the method for producing purified platelets of the present invention.

Also, the present invention is directed to a method for producing a blood product, including a blood product producing step of producing a blood product by mixing purified platelets and other components,
  wherein the purified platelets are obtained using the method for producing purified platelets of the present invention.

In order to achieve the second object, the present invention is directed to a platelet preserving solution containing albumin (hereinafter, alternatively referred to as a "preserving solution").

Also, the present invention is directed to a platelet preserving agent containing albumin (hereinafter, alternatively referred to as a "preserving agent").

Also, the present invention is directed to a method for preserving platelets (hereinafter, alternatively referred to as a "method for preserving"), including a preserving step of preserving platelets in the presence of albumin.

Advantageous Effects of Invention

According to the present invention, damage to platelets is suppressed compared with the above-described method, and purified platelets can be produced in a shorter period of time compared with the time that is taken to perform the above-described method so as to reduce damage to platelets. Furthermore, according to the present invention, platelets can be preferably preserved.

BRIEF DESCRIPTION OF DRAWINGS

FIG. 1 is a schematic diagram showing a concentration system in Example 1.

DESCRIPTION OF EMBODIMENTS

Method for Producing Purified Platelets

As described above, the method for producing purified platelets of the present invention is characterized by including a concentrating step of concentrating a megakaryocyte culture, and a centrifuging step of centrifuging platelets from an obtained concentrate. The method for producing platelets of the present invention is characterized in that, in the centrifuging step, platelets are centrifuged from a concentrate obtained in the concentrating step, and there is no particular limitation on other configurations and conditions. For example, the description of a later-described method for producing a platelet product and method for producing a blood product of the present invention is applicable to the method for producing platelets of the present invention.

According to the method for producing platelets of the present invention, the megakaryocyte culture is concentrated before the platelets are separated. Therefore, according to the method for producing platelets of the present invention, it is possible to reduce the volume of a sample (e.g., a concentrate) subjected to the centrifuging step. Therefore, according to the method for producing platelets of the present invention, the time necessary to separate the platelets in the centrifuging step can be shortened, and the time that is taken to purify platelets from the megakaryocyte culture can be shortened, and thus it is possible to obtain platelets in a shorter period of time compared with the above-described method. Furthermore, according to the method for producing platelets of the present invention, when separating platelets, it is not necessary to treat a large amount of megakaryocyte culture in separation through filtering, and thus, for example, damage to platelets that may occur when the flow rate is increased in the above-described method can be avoided. Therefore, according to the method for producing platelets of the present invention, damage to platelets is suppressed compared with the above-described method.

In the present invention, a "megakaryocyte" is the largest cell in bone marrow in a living body, and means a cell that releases platelets or functions in an equivalent manner. The cell that functions in an equivalent manner means a cell that can produce platelets. In the present invention, a megakaryocyte may be a megakaryocyte before multinucleation (polyploidization), that is, an immature megakaryocyte or a megakaryocyte in the growth phase, or a megakaryocyte after multinucleation (multinucleated megakaryocyte). Specific examples of the megakaryocyte include a promegakaryoblast, a megakaryoblast, a promegakaryocyte, and a mature megakaryocyte. It is sufficient that the number of sets of chromosomes included in the megakaryocyte after multinucleation is more than two, and is specifically 16 to 32, for example.

There is no particular limitation on the source from which the megakaryocytes are derived, and examples thereof include human and non-human animals. Examples of the non-human animals include primates such as monkeys, gorillas, chimpanzees, and marmosets, mice, rats, dogs, cats, rabbits, sheep, horses, and guinea pigs.

In the present invention, the megakaryocytes can be specified by a cell surface marker. If megakaryocytes are human derived, the cell surface marker may be CD41a, CD42a, and CD42b. That is to say, the megakaryocytes are cells that are positive for CD41a, CD42a, and CD42b. If megakaryocytes are human derived, the cell surface marker may be, for example, at least one selected from the group consisting of CD9, CD61, CD62p, CD42c, CD42d, CD49f, CD51, CD110, CD123, CD131, and CD203c.

In the present invention, a "platelet" is one of the cell components in blood, and is a cell component that is positive for CD41a and CD42b. A platelet does not have, for example, a cell nucleus, and, furthermore, is smaller than a megakaryocyte. Therefore, a platelet and a megakaryocyte can be distinguished from each other, for example, according to whether or not there is a cell nucleus and/or the size. It is known that a platelet plays an important role in forming a blood clot and stopping bleeding, and relates to regeneration of damaged tissues and physiological processes of inflammation. Furthermore, it is known that, when platelets are activated through bleeding or the like, receptors of cell integrins such as Integrin αIIBβ3 (glycoprotein IIb/IIIa; a complex of CD41a and CD61) are expressed on membranes of the platelets. Furthermore, when platelets are activated, the platelets aggregate and fibrin coagulates due to various blood coagulation factors released from the platelets, and thus blood clots are formed to facilitate stop of bleeding. In the present invention, the source from which the platelets are derived is the same as the source from which the megakaryocytes are derived.

It is known that damaged platelets become abnormal platelets. In such abnormal platelets, phosphatidylserines, which are negatively charged phospholipids, are exposed to the outside from the inside of the lipid bilayer. It is known that, in a living body, phosphatidylserines become exposed on the surface in accordance with activation of platelets, and many blood coagulation factors bind thereto, and thus the blood coagulation cascade is amplified. Meanwhile, in the abnormal platelets, many phosphatidylserines are always exposed on the surface, and thus, if abnormal platelets are administered to a patient, excessive blood coagulation occurs, which may result in a serious pathological condition such as disseminated intravascular coagulation. Furthermore, Annexin V binds to phosphatidylserines. Phosphatidylserines on the platelet surface can be detected, for example, using a flow cytometer using, as an indicator, the binding amount of fluorescence-labeled Annexin V. Therefore, damage to platelets can be evaluated as a change in the Annexin V positive rate in platelet fractions, that is, a change in the percentage or the number of platelets to which Annexin binds. Specifically, for example, if platelets are damaged during purification, the Annexin V positive rate in the platelets after the purification increases compared with the Annexin V positive rate before the purification.

In the present invention, the bioactivity of platelets can be evaluated using a known method. The bioactivity of platelets can be evaluated as the amount of activated platelets, for example, using an antibody for PAC-1 that specifically binds to Integrin αIIβ3 on membranes of activated platelets. Furthermore, the bioactivity of platelets may also be evaluated as the amount of activated platelets, for example, by detecting CD62p (P-selectin), which is a platelet activation marker, using an antibody. The bioactivity of platelets may also be evaluated, for example, through flow cytometry, by performing gating using an antibody for an activation-independent platelet marker CD61 or CD41, and then detecting the binding of an anti-PAC-1 antibody or an anti-CD62p antibody. The bioactivity of platelets may also be evaluated in the presence of adenosine diphosphate (ADP).

In the present invention, the bioactivity of platelets may be evaluated, for example, based on whether or not the platelets bind to fibrinogen in the presence of ADP. When platelets bind to fibrinogen, integrin that is necessary in the early stage of formation of a blood clot is activated. Moreover, the bioactivity of platelets may be observed, for example, by visualizing formation of a blood clot in vivo as shown in FIG. 6 of WO 2011/034073.

For example, if platelets have a low CD42b expression percentage or a low Annexin V positive rate, the platelets can be evaluated as having deteriorated or being abnormal (hereinafter, these states may be collectively referred to as "deterioration"), that is, a bioactivity of the platelets can be evaluated as being low. Platelets that have deteriorated do not have, for example, a sufficient function of forming a blood clot (blood coagulating function) or stopping bleeding, and thus the clinical usefulness thereof is low.

In the present invention, the "deterioration of platelets" means a decrease in CD42b (GPIbα) on the platelet surface. Therefore, platelets that have deteriorated include, for example, platelets in which the CD42b expression has been lowered, and platelets in which the extracellular region of CD42b has been cleaved through a shedding reaction. When CD42b is no longer present on the platelet surface, association with von Willebrand factor (VWF) does not occur, and thus the blood coagulating function of platelets is lost. The deterioration of platelets can be evaluated using, as an indicator, the CD42b negative rate (or the number of CD42b negative particles) with respect to the CD42b positive rate (or the number of CD42b positive particles) in platelet fractions. The higher the CD42b negative rate with respect to the CD42b positive rate is or the larger the number of CD42b negative particles with respect to the number of CD42b positive particles is, the more the platelets are evaluated as having deteriorated. The CD42b positive rate means the percentage of platelets to which an anti-CD42b antibody can bind, with respect to the platelets contained in the platelet fractions, and the CD42b negative rate means the percentage of platelets to which an anti-CD42b antibody cannot bind, with respect to the platelets contained in the platelet fractions.

The megakaryocyte culture can be produced, for example, by culturing megakaryocytes. Therefore, the method for producing platelets of the present invention may include, for example, before the concentrating step, a producing step of producing a megakaryocyte culture. The producing step can be performed, for example, by culturing the megakaryocytes in the presence of a medium. The megakaryocytes may be cultured, for example, on feeder cells, or without feeder cells. The megakaryocytes can be cultured, for example, through float culturing, and thus they can be cultured without feeder cells. The megakaryocyte culture includes platelets described above.

In the producing step, there is no particular limitation on the culturing conditions of the megakaryocytes, and ordinary culturing conditions of the megakaryocytes may be adopted. Specifically, for example, the culturing temperature is, for example, about 35 to about 42° C., about 36 to about 40° C., or about 37 to about 39° C. The $CO_2$ concentration is, for example, about 5 to about 15%. The $O_2$ concentration is, for example, about 15 to about 25%, or about 20%.

There is no particular limitation on the medium, and examples thereof include known media suited to produce platelets from the megakaryocytes, and equivalent media. Specifically, the medium can be prepared, for example, using, as a basal medium, a medium that is used to culture animal cells. Examples of the basal medium include single media such as an IMDM medium, a Medium 199 medium, an Eagle's Minimum Essential Medium (EMEM) medium, an αMEM medium, a Dulbecco's modified Eagle's Medium (DMEM), a Ham's F12 medium, a RPMI1640 medium, a Fischer's medium, and a Neurobasal (registered trademark) Medium (manufactured by Thermo Fisher Scientific), and mixed media thereof. The medium may contain, for example, serum or plasma, or may be a non-serum medium without containing them. The source from which the serum and plasma are derived is preferably the same as the source from which the megakaryocytes are derived. Specifically, for example, if the megakaryocytes are human derived, both the serum and the plasma are preferably human derived.

The medium may contain, for example, other components. There is no particular limitation on the other components, and examples thereof include albumin, insulin, transferrin, selenium, fatty acid, microelements, 2-mercaptoethanol, thiolglycerol, monothioglycerol (MTG), lipid, amino acid (e.g., L-glutamine), ascorbic acid, heparin, non-essential amino acid, vitamins, growth factor, low molecular weight compound, antibiotic, antioxidant, pyruvic acid, buffer, inorganic salts, cytokine, and the like. These other components may be contained, for example, alone or in combination of two or more. The cytokine is, for example, a substance that facilitates differentiation of blood cells, and specific examples thereof include a vascular endothelial growth factor (VEGF), thrombopoietin (TPO), various TPO-like agonists, a stem cell factor (SCF), an ITS (insulin-transferrin-selenite) supplement, an ADAM inhibitor, an FLT inhibitor, a WNT inhibitor, a ROCK inhibitor, an aryl hydrocarbon receptor (AhR) inhibitor, and the like. It is preferable that the medium is, for example, an IMDM medium containing serum, insulin, transferrin, serine, thiolglycerol, ascorbic acid, and TPO. For example, the medium may further contain SCF, and may further contain heparin. There is no particular limitation on the concentrations of the other components. The concentration of the TPO is, for example, about 10 ng/mL to about 200 ng/mL, or about 50 ng/mL to about 100 ng/mL. The concentration of the SCF is, for example, about 10 ng/mL to about 200 ng/mL, or about 50 ng/mL. The concentration of the heparin is, for example, about 10 U/mL to about 100 U/mL, or about 25 U/mL. The medium may further contain, for example, a phorbol ester (e.g., phorbol-12-myristate-13-acetate; PMA).

The megakaryocytes can be induced from, for example, cells that are more undifferentiated than megakaryocytes. Therefore, the method for producing platelets of the present invention may include, for example, before the production of a megakaryocyte culture, a megakaryocyte inducing step of inducing megakaryocytes from cells that are more undifferentiated than the megakaryocytes.

The "cells that are more undifferentiated than megakaryocytes" means cells having a potential to be differentiated into megakaryocytes. Specifically, for example, the cells that are more undifferentiated than megakaryocytes are, for example, hematopoietic stem cells, hematopoietic progenitors, CD34 positive cells, megakaryocyte-erythroid progenitors (MEP), megakaryocyte progenitors, and the like. The cells that are more undifferentiated than megakaryocytes may be isolated from, for example, bone marrow, cord blood, peripheral blood, or the like, or may be isolated from pluripotent cells such as embryonic stem cells (ES cell), induced pluripotent stem cells (iPS cells), nuclear transfer ES cells (ntES cells), germinal stem cells, somatic stem cells, embryonal carcinoma cells, or the like.

There is no particular limitation on the method for inducing megakaryocytes, and known inducing methods may be used. Specifically, for example, the method for inducing megakaryocytes may be, for example, the methods described in WO 2011/034073, WO 2012/157586, or the like. Specifically, for example, in the megakaryocyte inducing step, for example, an oncogene and a polycomb gene may be forcibly expressed in the cells that are more undifferentiated than megakaryocytes. Accordingly, in the megakaryocyte inducing step, for example, immortalized megakaryocytes that infinitely proliferate can be obtained. Moreover, for example, if the forced expression in the immortalized megakaryocytes is canceled, the immortalized megakaryocytes can be induced to multinucleated megakaryocytes, and platelets can be produced. Furthermore, in the megakaryocyte inducing step, for example, an apoptosis suppressor may be forcibly expressed in the megakaryocyte progenitors. Accordingly, in the megakaryocyte inducing step, the immortalized megakaryocytes can be obtained. Moreover, for example, if the forced expression in the immortalized megakaryocytes is canceled, multinucleated megakaryocytes can be induced from the immortalized megakaryocytes, and platelets can be produced.

In the megakaryocyte inducing step, for example, the oncogene, the polycomb gene, and the apoptosis suppressor may be forcibly expressed. In this case, the oncogene, the polycomb gene, and the apoptosis suppressor may be forcibly expressed simultaneously or at different times. Specifically, for example, in the megakaryocyte inducing step, a procedure may be employed in which, after the oncogene and the polycomb gene are forcibly expressed, the forced expression is canceled, and then the apoptosis suppressor is forcibly expressed, in which the oncogene, the polycomb gene, and the apoptosis suppressor are forcibly expressed, or in which the oncogene and the polycomb gene are forcibly expressed, and the apoptosis suppressor is expressed. Accordingly, in the megakaryocyte inducing step, the immortalized megakaryocytes can be obtained. Moreover, for example, if the forced expression in the immortalized megakaryocytes is canceled, multinucleated megakaryocytes can be induced from the immortalized megakaryocytes, and platelets can be produced.

In order to improve the efficiency in introducing the genes, for example, the megakaryocyte inducing step preferably includes a first expressing step of forcibly expressing an oncogene and a polycomb gene in the cells that are more undifferentiated than megakaryocytes, a second expressing step of forcibly expressing an apoptosis suppressor such as a Bcl-xL gene in the undifferentiated cells, and a canceling step of canceling all the forced expressions.

The genes can be forcibly expressed and the forced expression can be canceled, for example, using known methods such as the methods described in WO 2011/034073, WO 2012/157586, WO 2014/123242, or Reference Document 1 below, or equivalent methods. Specifically, for example, the genes can be forcibly expressed and the forced expression can be canceled, for example, using a drug-responsive gene expression inducing system. Examples of the gene expression inducing system include a Tet-on (registered trademark) system, a Tet-off (registered trademark) system, and the like. When the Tet-on system is used, for example, in the forcibly expressing step, culturing is performed in the presence of a drug that induces gene expression, such as tetracycline or doxycycline, and, in the step of canceling the forced expressions, the culturing is performed in the absence of the drug.

Reference Document 1: Nakamura S et al, "Expandable megakaryocyte cell lines enable clinically applicable generation of platelets from human induced pluripotent stem cells.", Cell Stem Cell, 2014, vol. 14, No. 4, pages 535-548

In the present invention, the "oncogene" means a gene that can induce carcinogenesis of cells in a living body, and examples thereof include MYC family genes such as c-MYC, N-MYC, and L-MYC, SRC family genes, RAS family genes, RAF family genes, protein kinase family genes such as c-kit (CD117), PDGFR (platelet growth factor receptor), and Abl (Abelson murine leukemia viral oncogene homolog), and the like.

In the present invention, the "polycomb gene" means a gene that is known to function to negatively control CDKN2a (cyclin-dependent kinase inhibitor 2A, INK4a/ARF), thereby avoiding cellular aging (Reference Documents 2 to 4 below). Specific examples of the polycomb gene include BMI1 (Polycomb complex protein BMI-1, polycomb group RING finger protein 4 (PCGF4), RING finger protein 51 (RNF51)), Me118 (Polycomb group RING finger protein 2), Ring (Ring Finger Protein) 1a/b, Phc (Polyhomeotic Homolog) 1/2/3, Cbx (Chromobox) 2/4/6/7/8, Ezh2 (Enhancer Of Zeste 2 Polycomb Repressive Complex 2 Subunit), Eed (Embryonic Ectoderm Development), Suz12 (SUZ12 Polycomb Repressive Complex 2 Subunit), HADC (Histone deacetylases), Dnmt (DNA (cytosine-5)-methyltransferase)1/3a/3b, and the like.

Reference Document 2: Hideyuki Oguro et al, "Senescence and Ageing of Stem Cells Regulated by Polycomb Complexes", Regenerative Medicine, 2007, vol. 6, No. 4, pages 26-32

Reference Document 3: Jesus Gil et.al, "Regulation of the INK4b-ARF-INK4a tumour suppressor locus: all for one or one for all", Nature Reviews Molecular Cell Biology, 2007, vol. 7, pages 667-677

Reference Document 4: Soo-Hyun Kim et.al., "Absence of $p16^{INK4a}$ and truncation of ARF tumor suppressors in chickens", PNAS, 2003, vol. 100, No. 1, pages 211-216

In the present invention, the "apoptosis suppressor" means a gene having a function that can suppress cellular apoptosis, and examples thereof include BCL2 (B-cell lymphoma 2), Bcl-xL (B-cell lymphoma-extra large), Survivin (Baculoviral IAP Repeat Containing 5), MCL1 (BCL2 Family Apoptosis Regulator), and the like.

As described above, the concentrating step is a step of concentrating the megakaryocyte culture. As described above, the megakaryocyte culture contains platelets. Furthermore, for example, the megakaryocyte culture is a mixed fluid containing solid fractions such as the megakaryocytes and the platelets, and liquid fractions such as the medium. Therefore, in the concentrating step, for example, solid fractions in the megakaryocyte culture, specifically, platelets are concentrated. Accordingly, in the concentrating step, for example, a concentrate containing the platelets can be obtained. There is no particular limitation on the method for concentrating the megakaryocyte culture, and, for example, known methods that can concentrate platelets may be used. Specifically, for example, the concentrating step can be performed, for example, using known solid-liquid separating methods. Specifically, this step can be performed, for example, using a concentrating member, or through centrifuge or the like. There is no particular limitation on the concentrating member, and examples thereof include known concentrating members suited to concentrate platelets. The concentrating member may be a hollow fiber membrane, a porous structure, or the like. The pore size of the concentrating member is, for example, a pore size that makes it possible to capture platelets. There is no particular limitation on the type of hollow fiber membrane, and the hollow fiber membrane may be, for example, a hollow fiber membrane made of polyethylene or the like, and, specifically, for example, it may be a Plasmaflo OP (Asahi Kasei Medical Co., Ltd.) or the like. If the megakaryocyte culture is concentrated using the hollow fiber membrane, the megakaryocyte culture is preferably concentrated through cross-flow treatment.

If the concentrating member is used, the concentrating step can be performed, for example, using a concentrating device including a culture vessel containing a megakaryocyte culture, the concentrating member, an inlet pipe, and an outlet pipe, wherein the culture vessel and a fluid inlet portion of the concentrating member are connected to the inlet pipe, and the culture vessel and a fluid outlet portion of the concentrating member are connected to the outlet pipe. If a hollow fiber membrane is used as the concentrating member, the fluid inlet portion can, for example, introduce the megakaryocyte culture into the hollow fiber membrane, and the fluid outlet portion can, for example, deliver a concentrate inside the hollow fiber membrane to the outlet pipe. In the concentrating step, for example, in the concentrating device, a megakaryocyte culture in the culture vessel is introduced via the inlet pipe and the fluid inlet portion of the concentrating member to the concentrating member, so that the megakaryocyte culture is concentrated, and the obtained concentrate is delivered via the fluid outlet portion of the concentrating member and the outlet pipe to the culture vessel, so that a concentrate of the megakaryocyte culture can be obtained. The megakaryocyte culture can be introduced and delivered, for example, using a fluid sending unit such as a pump. In the concentrating device, the megakaryocyte culture may be introduced and delivered to the concentrating member once or a plurality of times. In the case of the latter, the concentrating step can be said to be, for example, a step of circulating the megakaryocyte culture in the concentrating device. For example, a configuration may be employed in which the concentrating device further includes a fluid discharge vessel and a fluid discharge pipe, wherein the fluid discharge vessel and a fluid discharge portion of the concentrating member are connected to each other via the above-described fluid discharge pipe. If a hollow fiber membrane is used as the concentrating member, the fluid discharge portion can, for example, deliver a waste fluid outside the hollow fiber membrane to the fluid discharge pipe. In this case, in the concentrating step, for example, the waste fluid is delivered to the fluid discharge vessel in parallel with the concentration of the megakaryocyte culture.

There is no particular limitation on the concentration factor of the megakaryocyte culture in the concentrating step, and, for example, it is 5 to 20 times, or 10 to 20 times. The concentration factor can be calculated using Equation (1) below. As described later, if separated components after the separating step are concentrated, the concentration factor of the megakaryocyte culture in the concentrating step is, for example, 5 to 20 times, or 10 to 20 times.

$$M_c = V_b/V_a \quad (1)$$

$M_c$: Concentration factor
$V_a$: Volume (L) of megakaryocyte culture after concentration (concentrate)
$V_b$: Volume (L) of megakaryocyte culture before concentration As described above, the centrifuging step is a step of centrifuging platelets from the obtained concentrate. There is no particular limitation on the methods and conditions for centrifuging platelets, and known centrifuge method and centrifuge conditions used to centrifuge platelets may be used. The centrifuging step may include, for example, a step of centrifuging the concentrate a plurality of times at different centrifugal forces. If centrifugation is performed a plurality of times in the centrifuging step, the centrifuging step includes, for example, a first centrifuging step of separating megakaryocytes and platelets in the megakaryocyte culture through centrifugation, and a second centrifuging step of purifying the platelets through centrifugation from fractions containing the platelets after the first centrifuging step. Specifically, for example, the centrifuging step preferably includes a first centrifuging step of performing separation at a centrifugal force of about 150 to about 550×g (g: acceleration of gravity), and a second centrifuging step of separating liquid components collected in the first centrifuging step, at a centrifugal force of about 600 to about 4000×g. The centrifuging step can be performed, for example, using a known centrifugal separator. Therefore, the centrifugal force in the first and second centrifuging steps can be calculated using Equation (2) below, based on the number of rotations and the rotational radius of a rotor of a centrifugal separator that performs centrifugation.

$$RCF = 1119 \times r \times N^2 \times 10^{-8} \ (\times g) \quad (2)$$

RCF: Centrifugal force (relative centrifugal acceleration)
r: Maximum value of rotational radius (cm)
N: Number of rotations (rpm)

It is sufficient that the centrifugal force in the first centrifuging step is about 150 to about 550×g, and, from the viewpoint of suppressing shear stress on platelets due to deposition of solid fractions such as the megakaryocytes and the platelets, and more reliably suppressing expression of bioactivity of platelets due to shear stress, it is preferably about 160 to about 500×g, and more preferably about 170 to about 400×g. In the first centrifuging step, for example, a platelet preserving solution may be added to the megakaryocyte culture. Examples of the platelet preserving solution include a blood preserving solution A as defined by Minimum Requirements for Biological Products (Acid-Citrate-Dextrose; ACD-A), a Bicanate injection containing human serum albumin and an ACD-A solution, and the like. As the platelet preserving solution, it is preferable to use a later-described preserving solution of the present invention. The ACD-A solution has, for example, a blood/platelet anticoagulant action, and functions also as a glucose supply source that is an energy source of platelets.

It is sufficient that the centrifugal force in the second centrifuging step is about 600 to about 4000×g, and, from the viewpoint of suppressing deactivation of platelets, it is preferably about 800 to about 3000×g, and more preferably about 1000 to about 2000×g.

As described above, the centrifuging step can be performed, for example, using a known centrifugal separator. There is no particular limitation on the type of rotor used in the centrifugal separator, and the rotor may be, for example, an angle rotor, a swing rotor, a batch rotor, a continuous rotor, an elutriator rotor, or the like. For example, from the viewpoint of suppressing damage to platelets in the centrifuging step, the centrifugal separator is preferably a centrifugal separator including: a rotatable separator bowl having an inner wall to which a component with a large specific gravity in the concentrate or the collected liquid components (hereinafter, alternatively referred to as a "concentrate, etc.") is attached according to a centrifugal force, and an outlet port through which liquid components after separation of the concentrate, etc. flow out according to the centrifugal force; and a collecting unit for collecting the liquid components that have flowed out from the outlet port. In the separator bowl, when an axis that passes through the center of the bottom face of the separator bowl and is perpendicular to the bottom face is taken as the center, for example, the inner wall is arranged closer to the outer side than the outlet port is. If the separator bowl has a storage vessel in which the concentrate, etc. that has been introduced can be stored, the inner wall may be an inner wall of the storage vessel. Furthermore, if the separator bowl has such a storage vessel, when an axis that is perpendicular to the bottom face is taken as the center, the concentrate, etc. is preferably introduced from the outer side to the storage vessel. That is to say, the inlet port of the concentrate, etc. is preferably connected on the outer side of the storage vessel. Specific examples of the centrifugal separator include the apparatuses described in JP 2005-296675A and JP H7-284529A. Furthermore, as the centrifugal separator, for example, it is possible to use a commercially available centrifugal separator that is used to separate blood components, a commercially available apparatus that is used to wash platelets of a platelet concentrate product, and the like. Examples of the commercially available apparatuses include an ACP215 manufactured by Haemonetics, COBE2991 manufactured by Terumo Corporation, and the like.

According to the centrifugal separator including the separator bowl, for example, when the concentrate, etc. is introduced while the separator bowl is being rotated about an axis that passes through the center of the bottom face and is perpendicular to the bottom face, according to the centrifugal force, a component with a large specific gravity is attached to and deposited on the inner wall of the separator bowl, and a component with a small specific gravity remains in the fluid. Therefore, if centrifugation is performed using the centrifugal separator including the separator bowl, by introducing the concentrate, etc. to the separator bowl at a predetermined speed, and, at the same time, the separated liquid components are collected by the collecting unit, for example, regardless of the capacity of the separator bowl, a large amount of concentrate or collected liquid components can be continuously separated. In the first centrifuging step, the component with a large specific gravity is, for example, megakaryocytes, and the component with a small specific gravity is, for example, platelets. Furthermore, in the second centrifuging step, the component with a large specific gravity is, for example, platelets, and the component with a small specific gravity is, for example, other components such as proteins.

In the centrifugal separator, the liquid components containing the component with a small specific gravity and the component with a large specific gravity can be collected by, for example, the collecting unit. The collecting unit includes, for example, a tubular member such as a tube connected to the outlet port of the separator bowl, and a collecting bag replaceably connected to the tubular member. There is no limitation on the collecting bag, as long as, for example, the quality of platelets is not affected, and it is possible to use, for example, commercially available blood preservation bag, blood component preservation bag, or the like.

When the centrifugal separator including the separator bowl is used, the first centrifuging step can be performed, for example, by rotating the separator bowl at the above-described centrifugal force. Specifically, the first centrifuging step is performed, for example, by introducing the concentrate to the separator bowl while rotating the separator bowl at the above-described centrifugal force. Accordingly, for example, the megakaryocytes and the platelets can be separated from each other. Furthermore, after the first centrifuging step, for example, the megakaryocytes are attached to the inner wall of the separator bowl, and the platelets remain in the liquid components after separation. Therefore, for example, when the liquid components in the separator bowl are collected in the collecting bag or the like using the collecting unit, liquid components containing platelets can be collected. Then, the liquid components containing platelets are subjected to the second centrifuging step, for example, as liquid components collected in the first centrifuging step.

In the first centrifuging step, there is no particular limitation on the method for the megakaryocyte culture to the separator bowl, and, for example, it is possible to use a fluid sending unit such as a pump included in the centrifugal separator, or to connect a container containing the megakaryocyte culture and the separator bowl via a tube, suspend the container at a high position, and allow the megakaryocyte culture to naturally fall via the tube into the separator bowl. There is no particular limitation on the introduction speed of the megakaryocyte culture, and, for example, it is about 50 to about 150 mL/min, about 80 to about 130 mL/min, or about 100 mL/min. There is no particular limitation on the temperature at which the first centrifuging step is performed, and, for example, it is room temperature (e.g., around 25° C.). Furthermore, there is no particular limitation on the centrifugation time in the first centrifuging step, and, for example, it is a period of time that is greater than or equal to the time obtained by dividing the volume of the megakaryocyte culture by the introduction speed of the megakaryocyte culture.

After the first centrifuging step, for example, the separator bowl may be replaced or washed. Then, the second centrifuging step is performed. The second centrifuging step can be performed, for example, by rotating the separator bowl at the above-described centrifugal force. Specifically, the second centrifuging step is performed, for example, by introducing the liquid components collected in the first separating step to the separator bowl while rotating the separator bowl at the above-described centrifugal force. Accordingly, the platelets can be separated from the collected liquid components.

In the second centrifuging step, there is no particular limitation on the method for introducing the collected liquid components to the separator bowl, and, for example, it may be performed in a similar way to that of the first centrifuging step, or to suspend a collecting bag containing the collected liquid components obtained in the first centrifuging step at a high position, and introduce the liquid components to the separator bowl by allowing them to naturally fall via a tubular member. There is no particular limitation on the introduction speed of the collected liquid components, and, for example, the description of the introduction speed of the megakaryocyte culture is applicable thereto. There is no particular limitation on the temperature at which the second centrifuging step is performed, and, for example, it is room temperature (e.g., around 25° C.). Furthermore, there is no particular limitation on the centrifugation time in the second centrifuging step, and, for example, it is a period of time that is greater than or equal to the time obtained by dividing the volume of the collected liquid components by the introduction speed of the collected liquid components.

For example, the method for producing platelets of the present invention may further include a collecting step of collecting platelets after centrifugation. There is no particular limitation on the collecting method, and the method can be performed by collected liquid fractions (liquid components) or solid fractions (solid components) containing platelets according to the centrifuging conditions in the centrifuging step.

When the centrifugal separator including the separator bowl is used, after the second centrifuging step, for example, the platelets are attached to the inner wall of the separator bowl, and the other components remain in the liquid components after separation. Therefore, in the collecting step, for example, first, the liquid components in the separator bowl are collected using the collecting unit. Next, in the collecting step, for example, the separator bowl is swung. Accordingly, the platelets are shaken off the separator bowl, and, for example, are suspended in liquid components such as a washing and preserving solution (e.g., remaining washing and preserving solution) that is present in the separator bowl. Then, in the collecting step, for example, the platelets are collected by applying pressure from the outlet port of the separator bowl, and delivering the washing and preserving solution from the inlet port of the separator bowl. Specifically, in the collecting step, for example, the platelets are collected by introducing a gas such as air from the outlet port of the separator bowl. More specifically, a gas such as air is introduced from the outlet port of the separator bowl, and liquid components such as the washing and preserving solution containing the platelets are collected from the inlet port of the separator bowl. Note that the washing and preserving solution that is present after collecting the liquid components in the separator bowl may be, for example, a washing and preserving solution remaining in the separator bowl after collecting the liquid components, a washing and preserving solution introduced after collecting the liquid components, or a mixed fluid thereof. Furthermore, if the separator bowl has an inlet port for the washing and preserving solution, the platelets may be collected, for example, from the inlet port for the washing and preserving solution. Examples of the washing and preserving solution include a bicarbonate Ringer's solution such as a Bicarbon infusion. For example, the washing and preserving solution may further contain a platelet preserving solution (ACD), albumin, and the like, and, specifically, for example, it may contain 5 to 20 (v/v)% of ACD and 2.5 to 10 (w/v)% of albumin. From the viewpoint of suppressing deterioration in platelets in the first and second separating steps, for example, the washing and preserving solution is preferably a later-described preserving solution of the present invention.

The method for producing platelets of the present invention may include, for example, after the second centrifuging step, a washing step of performing washing by adding a washing and preserving solution to the separator bowl and rotating the separator bowl. In this case, for example, the method for producing platelets of the present invention may further include, after the washing step, a platelet collecting step of collecting platelets by adding a collected fluid to the separator bowl and rotating the separator bowl. Since the method for producing platelets of the present invention includes the washing step, for example, components such as the medium attached and deposited together with the platelets in the second centrifuging step can be removed. Furthermore, since the method for producing platelets of the present invention includes the washing step, for example, when performed in combination with a later-described platelet separating step, clogging of the separating member can be suppressed, and purified platelets can be produced in a shorter period of time.

In the washing step, for example, a washing and preserving solution is introduced to the separator bowl, and the separator bowl is rotated at a centrifugal force of about 600 to 3600×g. Accordingly, for example, the platelets are attached to the inner wall of the separator bowl, and the components such as a medium remain in the liquid components after washing. There is no particular limitation on the method for introducing the washing and preserving solution, and, for example, it may be performed in a similar way to that of the first and second centrifuging steps. There is no particular limitation on the introduction speed of the washing and preserving solution, and, for example, it is introduced at constant speed. Examples of the washing and preserving solution include a bicarbonate Ringer's solution such as a Bicarbon infusion. For example, the washing and preserving solution may further contain a platelet preserving solution (ACD-A), albumin, and the like, and, specifically, for example, it may contain 5 to 20 (v/v) % of ACD and 2.5 to 10 (w/v) % albumin.

Next, the platelet collecting step may be performed, for example, in a similar way to that of the collecting step.

The method for producing platelets of the present invention may include, for example, before the washing step, a separated component collecting step of collecting separated components in the separator bowl after the second centrifuging step. In this case, the method for producing platelets of the present invention includes, for example, a separated component concentrating step of concentrating the separated components. Furthermore, if the method for producing platelets of the present invention includes the separated component collecting step, it is preferable that, in the washing step, for example, washing is performed by adding concentrated separated components and a washing and preserving solution to the separator bowl and rotating the separator bowl.

In the separated component collecting step, the separated components are components attached to the inner wall of the separator bowl, and specific examples thereof include platelets. The separated component collecting step may be performed, for example, in a similar way to that of the collecting step.

The separated component concentrating step may be performed, for example, in a similar way to that of the concentrating step, except that collected separated components are used instead of the megakaryocyte culture. The separated component concentrating step is preferably performed using the above-described concentrating member. There is no particular limitation on the concentration factor of the collected separated components in the separated component concentrating step, and it is, for example, 5 to 20 times, or 10 to 20 times. The concentration factor can be calculated using Equation (1) above, while replacing "megakaryocyte culture" with "collected separated components".

The method for producing platelets of the present invention includes, for example, a platelet separating step of separating the platelets collected in the collecting step or the platelet collecting step described above, by causing the platelets to pass through a separating member. The platelets collected in the collecting step or the platelet collecting step may contain, for example, other blood cells such as megakaryocytes as well as the platelets. Therefore, since the method for producing platelets of the present invention includes the platelet separating step, for example, more reliably purified platelets can be obtained. Furthermore, according to the method for producing platelets of the present invention, for example, the amount of sample subjected to the separating member is made smaller compared with the above-described method. Therefore, according to the method for producing platelets of the present invention, a separating member with a smaller size may be used compared with the separating member used in the above-described method. There is no particular limitation on the separating member, and examples thereof include known separating members that can separate the platelets and other blood cells, such as a separating membrane made of a nonwoven fabric, a mesh material, or the like, a hollow fiber membrane, and a porous structure. The pore size of the separating member is, for example, a pore size that makes it possible to allow the platelets to pass through the separating member. For example, the above-described description is applicable to the hollow fiber membrane.

There is no particular limitation on the method for introducing collected platelets to the separating member in the platelet separating step, and, for example, they may be introduced using a fluid sending unit such as a pump or by allowing them to naturally fall, but the latter method is preferable because, when the separating member is clogged, an increase in the pressure to platelets is suppressed and damage to the platelets can be suppressed compared with the fluid sending method using the fluid sending unit.

In the method for producing platelets of the present invention, for example, separated platelets may be collected after the platelet separating step. Moreover, in the method for producing platelets of the present invention, for example, impurities in the separated platelets may be removed using a filter. In this manner, according to the method for producing platelets of the present invention, purified platelets can be produced.

Platelets

The platelets of the present invention are characterized by being obtained using the method for producing purified platelets of the present invention. The platelets of the present invention are characterized by being obtained using the method for producing platelets of the present invention, and there is no particular limitation on the other steps and conditions. For example, the description of the method for producing platelets of the present invention is applicable to the platelets of the present invention.

The platelets of the present invention may contain albumin. In this case, the platelets of the present invention include platelets and albumin. The description of albumin in a later-described preserving solution of the present invention is applicable to the albumin.

Method for Producing Platelet Product

As described above, the method for producing a platelet product of the present invention is characterized by including a product producing step of producing a platelet product from purified platelets, wherein the purified platelets are obtained using the method for producing purified platelets of the present invention. The method for producing a platelet product of the present invention is characterized in that the purified platelets are obtained using the method for producing platelets of the present invention, and there is no particular limitation on the other steps and conditions. The description of the method for producing platelets of the present invention is applicable to the method for producing a platelet product of the present invention.

In the product producing step, for example, other components may be added. Examples of the other components include stabilizers of cells such as platelets, and the like.

The method for producing a platelet product of the present invention may include, before the product producing step, a purified platelet producing step of producing purified platelets, using the method for producing platelets of the present invention. For example, the description of the method for producing platelets of the present invention is applicable to the purified platelet producing step.

Platelet Product

The platelet product of the present invention is characterized by being obtained using the method for producing a platelet product of the present invention. The platelet product of the present invention is characterized by being obtained using the method for producing a platelet product of the present invention, and there is no particular limitation on the other steps and conditions. For example, the description of the method for producing purified platelets of the present invention and the method for producing a platelet product is applicable to the platelet product of the present invention.

The platelet product of the present invention may contain albumin. In this case, the platelet product of the present invention contains platelets and albumin. The description of albumin in a later-described preserving solution of the present invention is applicable to the albumin.

Method for Producing Blood Product

As described above, the method for producing a blood product of the present invention is characterized by including a blood product producing step of producing a blood product by mixing purified platelets and other components, wherein the purified platelets are obtained using the method for producing purified platelets of the present invention. The method for producing a blood product of the present invention is characterized in that the purified platelets are obtained using the method for producing platelets of the present invention, and there is no particular limitation on the other steps and conditions. The description of the method for producing platelets of the present invention is applicable to the method for producing a blood product of the present invention.

There is no particular limitation on the other components, and examples thereof include stabilizers of other blood cells such as red blood cells, cells such as platelets, and the like.

The method for producing a blood product of the present invention may include, before the blood product producing step, a purified platelet producing step of producing purified platelets, using the method for producing platelets of the present invention. For example, the description of the method for producing platelets of the present invention is applicable to the purified platelet producing step.

Blood Product

The blood product of the present invention is characterized by being obtained using the method for producing a blood product of the present invention. The blood product of the present invention is characterized by being obtained using the method for producing a blood product of the present invention, and there is no particular limitation on the other steps and conditions. For example, the description of the method for producing purified platelets of the present invention and the method for producing a blood product is applicable to the blood product of the present invention.

Platelet Preserving Solution

As described above, the platelet preserving solution of the present invention is characterized by containing albumin. The preserving solution of the present invention is characterized by containing albumin, and there is no particular limitation on other configurations and conditions. For example, the description of the method for producing purified platelets of the present invention, and a later-described preserving agent and preserving method of the present invention is applicable to the platelet preserving solution of the present invention.

The present inventors conducted an in-depth study and found that, when platelets are preserved in the presence of albumin, a deterioration in platelets can be suppressed compared with the case in which platelets are preserved in the absence of albumin, and thus the present invention was achieved. Therefore, according to the present invention, platelets can be preferably preserved. Furthermore, the present inventors found that, when platelets are centrifuged in the presence of albumin, a deterioration in platelets can be suppressed compared with the case in which platelets are centrifuged in the absence of albumin. Therefore, according to the preserving solution of the present invention, a deterioration in platelets during centrifugation of the platelets can be suppressed, and it can be preferably used, for example, as a centrifugation solution for platelets, or a washing and preserving solution in the above-described method for producing purified platelets of the present invention.

Examples of the albumin include serum albumin, lactalbumin, and the like, and it is preferable to use serum albumin. There is no particular limitation on the source from which the albumin is derived, and, for example, the description of the source of the megakaryocytes is applicable thereto. The source from which the albumin is derived is preferably the same as the source from which the platelets are derived. Specifically, for example, if the platelets are human platelets, the albumin is preferably human albumin, and more preferably human serum albumin. Specifically, for example, the human serum albumin may be a protein constituted by an amino acid sequence registered with the NCBI Accession number NP_000468. The albumin may be, for example, purified from a biological sample such as blood, body fluids, or the like, or a recombinant protein. Furthermore, the albumin may be a commercially available product, or may be prepared in a laboratory.

In the preserving solution of the present invention, it is sufficient that the lower limit of the concentration of the albumin is more than 0 w/v % (weight/volume %). For example, from the viewpoint of more reliably suppressing a deterioration in platelets, it is preferably 1.25 w/v % or more, and, from the viewpoint of even more reliably suppressing a deterioration in platelets, it is more preferably 2.5 w/v % or more, and even more preferably 5 w/v % or more. There is no particular limitation on the upper limit of the concentration of the albumin, and, for example, it is 25 w/v % or less, or 20% or less. For example, from the viewpoint of improving the handleability during usage, it is preferably 15 w/v % or less, and, from the viewpoint of improving the handleability during administration, it is more preferably 10 w/v % or less. The range of the concentration of the albumin is, for example, more than 0 w/v % and 25 w/v % or less. For example, from the viewpoint of more reliably suppressing a deterioration in platelets and improving the handleability during usage, it is preferably 1.25 to 15 w/v %, more preferably 2.5 to 10 w/v %, and even more preferably 5 to 10 w/v %.

For example, from the viewpoint of providing an energy source for platelets and suppressing a deterioration in platelets, the preserving solution of the present invention preferably contains a sugar, and examples of the sugar include dextrose (glucose).

In the preserving solution of the present invention, the lower limit of the concentration of the sugar is, for example, 0.05 w/v %, or 0.1 w/v % or more, and preferably 0.104 w/v % or more. The upper limit of the concentration of the sugar is 0.2 w/v %, or 0.4 w/v % or less, and preferably 0.367 w/v % or less. The range of the concentration of the sugar is, for example, 0.05 to 0.8 w/v %, preferably 0.1 to 0.4 w/v %, and more preferably 0.104 to 0.367 w/v %.

The preserving solution of the present invention preferably contains, for example, an electrolyte. Examples of the electrolyte include sodium chloride, potassium chloride, calcium chloride, magnesium chloride, sodium hydrogen carbonate, sodium citrate, citric acid, and the like. For example, from the viewpoint of providing a blood/platelet anticoagulant action and suppressing a deterioration in platelets, the preserving solution of the present invention preferably contains sodium citrate, or citric acid. The preserving solution of the present invention may contain, for example, one electrolyte, or two or more electrolytes.

In the preserving solution of the present invention, there is no particular limitation on the concentration of the electrolyte, and it may be set as appropriate according to the type of electrolyte. The range of the concentration of the sodium chloride is, for example, 0.3 to 1.5 w/v %, 0.3 to 0.8 w/v %, or 0.4 to 0.6 w/v %, and preferably 0.48 to 0.56 w/v %, or 0.486 to 0.557 w/v %. The range of the concentration of the potassium chloride is, for example, 0.01 to 0.04 w/v %, or 0.02 to 0.03 w/v %, and preferably 0.025 to 0.028 w/v %, or 0.025 to 0.0286 w/v %. The range of the concentration of the calcium chloride dihydrate is, for example, 0.01 to 0.04 w/v %, or 0.015 to 0.03 w/v %, and preferably 0.018 to 0.025 w/v %, or 0.0183 to 0.021 w/v %. Note that, if calcium chloride, calcium chloride tetrahydrate, or calcium chloride hexahydrate is used instead of the calcium chloride dihydrate, the concentration thereof is preferably set to be equivalent to the above-described concentration of the calcium chloride dihydrate in the preserving solution. The range of the concentration of the magnesium chloride is, for example, 0.01 to 0.03 w/v %, or 0.015 to 0.02 w/v %, and preferably 0.016 to 0.019 w/v %, or 0.0167 to 0.019 w/v %. The range of the concentration of the sodium hydrogen carbonate is, for example, 0.1 to 0.3 w/v %, or 0.15 to 0.25 w/v %, and preferably 0.19 to 0.23 w/v %, or 0.195 to 0.224 w/v %. The range of the concentration of the sodium citrate dihydrate is, for example, 0.05 to 0.5 w/v %, or 0.1 to 0.4 w/v %, and preferably 0.12 to 0.39 w/v %, or 0.123 to 0.384 w/v %. Note that, if sodium citrate is used instead of the sodium citrate dihydrate, the concentration thereof is preferably set to be equivalent to the above-described concentration of the sodium citrate dihydrate in the preserving solution. The range of the concentration of the citric acid monohydrate is, for example, 0.01 to 0.15 w/v %, or 0.03 to 0.14 w/v %, and preferably 0.035 to 0.135 w/v %, or 0.038 to 0.134 w/v %. Note that, if citric acid is used instead of the citric acid monohydrate, the concentration thereof is preferably set to be equivalent to the above-described concentration of the citric acid monohydrate in the preserving solution.

The preserving solution of the present invention preferably contains the sugar and the electrolyte. In this case, the electrolyte preferably contains one, or two or more, of sodium chloride, potassium chloride, calcium chloride, magnesium chloride, sodium hydrogen carbonate, sodium citrate, and citric acid, and more preferably contains all of them. The description above is applicable to the concentrations of the sugar and the electrolyte, and any examples above may be used in combination.

The preserving solution of the present invention may contain, for example, platelets. In this case, the preserving solution of the present invention can be said to be, for example, a platelet product. For example, the platelets may contain only platelets, or also contain cell components other than platelets, wherein the case of the former is preferable. In the case of the former, the platelets can be obtained, for example, using the method for producing purified platelets of the present invention.

The preserving solution of the present invention may contain other components, instruction manuals, attached documents, and the like.

The preserving solution of the present invention may be contained, for example, in a bag such as an infusion bag, a blood bag, or the like.

The preserving solution of the present invention can be produced by mixing various components, or produced using a commercially available product. In the case of the latter, for example, the preserving solution of the present invention can be produced by mixing a bicarbonate Ringer's solution such as a Bicarbon infusion and albumin, or by mixing a bicarbonate Ringer's solution and a blood preserving solution such as an ADC-A solution and adding albumin to the mixture. Specifically, for example, if an ACD-A solution (manufactured by Terumo Corporation) is added to a Bicarbon infusion (manufactured by Otsuka Pharmaceutical Co., Ltd.), the preserving solution can be produced by adding the ACD-A solution, for example, such that a volume (Ac) of the ACD-A solution is, for example, $0 \times B \leq Ac \leq 0.2 \times B$, preferably $0.05 \leq B \leq Ac \leq 0.2 \times B$, and more preferably $0.1 \times B \leq Ac \leq 0.2 \times B$, with respect to a volume (B) of the Bicarbon infusion. Furthermore, if a human serum albumin product (albumin concentration 25 w/v % (e.g., Albuminar (registered trademark) 25%, manufactured by CSL Behring K.K.)) is added to a Bicarbon infusion (manufactured by Otsuka Pharmaceutical Co., Ltd.), the preserving solution can be produced by adding the human serum albumin product, for example, such that a volume (A1) of the human serum albumin product is, for example, $0 \times B < A1 \leq 0.25 \times B$, preferably $0.0125 \times B \leq A1 \leq 0.15 \times B$, and more preferably $0.025 \times B \leq A1 \leq 0.1 \leq B$ or $0.05 \leq B \leq A1 \leq 0.1 \times B$, with respect to a volume (B) of the Bicarbon infusion. Furthermore, the preserving solution can be produced by adding an ACD-A solution and a human serum albumin product to a Bicarbon infusion (manufactured by Otsuka Pharmaceutical Co., Ltd.). In this case, the description above is applicable to the proportions of the ACD-A solution and the human serum albumin product added.

Platelet Preserving Agent

As described above, the platelet preserving agent of the present invention is characterized by containing albumin. The preserving agent of the present invention is characterized by containing albumin, and there is no particular limitation on other configurations and conditions. According to the present invention, for example, a deterioration in platelets can be suppressed, and thus platelets can be preferably preserved. For example, the description of the method for producing purified platelets of the present invention, and a later-described preserving agent and preserving method of the present invention is applicable to the preserving agent of the present invention.

The albumin is preferably serum albumin. The content of the albumin may be set, for example, such that, when mixed with a predetermined amount of water, the concentration of the albumin in the preserving solution of the present invention is obtained.

The preserving agent of the present invention preferably contains a sugar, and more preferably dextrose. The content of the sugar may be set, for example, such that, when mixed with a predetermined amount (preset amount) of water, the concentration of the sugar in the preserving solution of the present invention is obtained.

The preserving agent of the present invention preferably contains an electrolyte. The electrolyte preferably contains one, or two or more, of sodium chloride, potassium chloride, calcium chloride, magnesium chloride, sodium hydrogen carbonate, sodium citrate, and citric acid, and more preferably contains all of them. The content of each electrolyte may be set, for example, such that, when mixed with a predetermined amount of water, the concentration of each electrolyte in the preserving solution of the present invention is obtained.

The preserving agent of the present invention preferably contains the sugar and the electrolyte.

If the preserving agent of the present invention contains a plurality of constituent elements, the constituent elements may be contained in the same container in a mixed state or unmixed state, or respectively contained in different containers. If the constituent elements are respectively contained in different containers, the preserving agent of the present invention can be said to be, for example, a preservation kit.

There is no particular limitation on the form of the preserving agent of the present invention, and examples thereof include a liquid form and a solid form.

Method for Preserving Platelets

As described above, the method for preserving platelets of the present invention is characterized by including a preserving step of preserving platelets in the presence of albumin. The preserving method of the present invention is characterized in that platelets are preserved in the presence of albumin, and there is no particular limitation on the other steps and conditions. According to the present invention, for example, a deterioration in platelets can be suppressed, and thus platelets can be preferably preserved. The description of the method for producing purified platelets, the preserving solution, and the preserving agent of the present invention is applicable to the preserving method of the present invention.

In the preserving step, platelets are preserved in the presence of albumin. Specifically, the preserving step can be performed, for example, by bringing platelets and the preserving solution of the present invention into contact with each other, and preserving the thus obtained mixed fluid. For example, the platelets may contain only platelets, or also contain cell components other than platelets, wherein the case of the former is preferable. In the case of the former, the platelets can be obtained, for example, using the method for producing purified platelets of the present invention. The albumin is preferably serum albumin. For example, the description of the concentration of the albumin in the preserving solution of the present invention is applicable to the concentration of the albumin.

There is no particular limitation on the preservation conditions of the platelets, and, for example, the conditions may be set as appropriate based on preservation conditions of known platelet products. The preservation temperature of platelets is, for example, 15 to 37° C., and preferably 20 to 24° C. The preservation time of the platelets is, for example, 0 to 14 days, preferably within 4 days. The pH of the platelets during preservation is, for example, pH 6.5 or more, and preferably pH 6.5 to 7.5. Furthermore, the platelets may be agitated by gently shaking a preservation container containing the platelets during preservation.

In the preserving method of the present invention, the preserving step is preferably performed in the presence of a sugar. The sugar is preferably dextrose. For example, the description of the concentration of the sugar in the preserving solution of the present invention is applicable to the concentration of the sugar.

In the preserving method of the present invention, the preserving step is preferably performed in the presence of an electrolyte. The electrolyte preferably contains one, or two or more, of sodium chloride, potassium chloride, calcium chloride, magnesium chloride, sodium hydrogen carbonate, sodium citrate, and citric acid, and more preferably contains all of them. For example, the description of the concentration of the electrolyte in the preserving solution of the present invention is applicable to the concentration of the electrolyte.

In the preserving method of the present invention, the preserving step is preferably performed in the presence of the sugar and the electrolyte.

Use for Preservation of Platelets

The present invention is directed to use of albumin for preservation of platelets, and use of albumin for preservation of a platelet product. For example, the description of the method for producing purified platelets of the present invention, the preserving solution, the preserving agent, and the preserving method is applicable to the present invention.

EXAMPLES

Hereinafter, the present invention will be described in detail by way of examples, but the present invention is not limited to the aspects described in the examples.

Example 1

It was checked whether or not, according to the method for producing platelets of the present invention, damage to platelets is suppressed compared with the above-described method.

(1) Production of Immortalized Megakaryocyte Cells

Immortalized megakaryocytes were produced as follows.

(1-1) Preparation of Hematopoietic Progenitors from iPS Cells

Differentiation culturing was performed to differentiate human iPS cells (TKDN SeV2 and NIH5: human fetal skin fibroblasts-derived iPS cells generated using Sendai virus) to blood cells, using the method described in Reference Document 5 below. Specifically, a human ES/iPS cell colony was co-cultured with C3H10T1/2 feeder cells in the presence of 20 ng/mL of VEGF (manufactured by R&D Systems) for 14 days, so that hematopoietic progenitors (Hematopoietic Progenitor Cells; HPC) were produced. The culturing conditions were 37° C., 20% $O_2$, 5% $CO_2$ (the same conditions were applied below unless otherwise described).

Reference Document 5: Takayama N. et al., "Transient activation of c-MYC expression is critical for efficient platelet generation from human induced pluripotent stem cells", J. Exp. Med., 2010, vo.13, pages 2817-2830

(1-2) Gene Introducing System

As the gene introducing system, a lentiviral vector system was used. A lentiviral vector is a tetracycline-controlled Tet-on (registered trademark) gene expression inducing system vector. It was produced by recombining an mOKS cassette of LV-TRE-mOKS-Ubc-tTA-I2G (Reference Document 6 below) with c-MYC, BMI1 or BCL-xL. The vectors to which c-MYC, BMI1, and BCL-xL were introduced were respectively taken as LV-TRE-c-Myc-Ubc-tTA-I2G, LVTRE-BMI1-Ubc-tTA-I2G, and LV-TRE-BCL-xL-Ubc-tTA-I2G. c-MYC, BMI1, and BCL-xL viruses were produced through gene introduction to 293T cells using the lentiviral vector. Target cells were infected with the obtained viruses, so that c-MYC, BMI1, and BCL-xL genes were introduced to the genomic sequences of the target cells. The genes stably introduced to the genomic sequences can be forcibly expressed by adding doxycycline (clontech #631311) to a medium.

Reference Document 6: Kobayashi, T.et al., "Generation of rat pancreas in mouse by interspecific blastocyst injection of pluripotent stem cells.", Cell, 2010, vol. 142, No. 5, pages 787-799

(1-3) Infection of Hematopoietic Progenitors with c-MYC and BMI1 Virus

HPC obtained using the method (1-1) was disseminated at $5 \times 10^4$ cells/well on a 6-well plate on which C3H10T1/2 feeder cells were disseminated in advance, and c-MYC and BMI1 were forcibly expressed using the lentiviral method using BMI1 virus and c-MYC virus. At that time, six wells were used for each type of cell line. Specifically, the virus particles were added to a medium each at an MOI (multiplicity of infection) of 20, and infection was caused through spin infection (32° C., 900 rpm, centrifugation for 60 minutes). The spin infection was performed twice every 12 hours. Human thrombopoietin (TPO) (R&D SYSTEMS), Human Stem Cell Factor (SCF) (R&D SYSTEMS), and Doxycycline (Dox, clontech #631311) were added respectively to concentrations of 50 ng/mL, 50 ng/mL, and 2 µg/mL to a basal medium (IMDM (Iscove's Modified Dulbecco's Medium) (Sigma-Aldrich) containing 15% Fetal Bovine Serum (GIBCO), 1% Penicillin-Streptomycin-Glutamine (GIBCO), 1% Insulin, Transferrin, Selenium Solution (ITS-G) (GIBCO), 0.45 mmol/L 1-Thioglycerol (Sigma-Aldrich), and 50 µg/mL L-Ascorbic Acid (Sigma-Aldrich)) to obtain a medium (hereinafter, referred to as a "differentiation medium"), and protamine was further added thereto to a final concentration of 10 µg/mL to obtain a medium used in the experiments.

(1-4) Production and Maintenance Culturing of Megakaryocytes Self-Propagating Strains While taking the date on which infection with c-MYC and BMI1 virus was caused using the method (1-3) as the $0^{th}$ day of infection, HPC to which c-MYC genes and BMI1 genes were introduced was cultured as follows, and thus megakaryocytes self-propagating strains were produced. Forced expression of c-MYC genes and BMI1 genes was performed by adding DOX to the medium to a concentration of 1 µg/mL.

$2^{nd}$ to $11^{th}$ Days of Infection

On the $2^{nd}$ day of infection, the virus-infected blood cells obtained as described above were collected through pipetting, subjected to centrifugation at 1200 rpm for 5 minutes for removing a supernatant, suspended in a new differentiation medium, and disseminated on new C3H10T1/2 feeder cells (6-well plate). On the $9^{th}$ day of infection, passage was performed by performing a similar operation. In the re-dissemination, the number of cells was counted, and then the cells were disseminated at 1×10⁵ cells/2 mL/well on C3H10T1/2 feeder cells (6-well plate).

12$^{th}$ to 13$^{th}$ Day of Infection

An operation similar to that on the 2$^{nd}$ day of infection was performed. After the number of cells was counted, the cells were disseminated at 3×10⁵ cells/10 mL/100-mm dish on C3H10T1/2 feeder cells (100-mm dish).

14$^{th}$ Day of Infection

The virus-infected blood cells were collected, and were reacted with 2 μL of anti-human CD41a-APC antibody (BioLegend), 1 μL of anti-human CD42b-PE antibody (eBioscience), and 1 μL of anti-human CD235ab-pacific blue (BioLegend) antibody per 1.0×10⁵ cells. After the reaction, analysis was performed using FACS Verse (trademark) (BD Biosciences). On the 14$^{th}$ day of infection, cells with a CD41a positive rate of 50% or more were taken as megakaryocytes self-propagating strains.

(1-5) Infection of Megakaryocytes Self-Propagating Strains with BCL-xL Virus

BCL-xL genes were introduced to the megakaryocytes self-propagating strains on the 14$^{th}$ day of infection, using the lentiviral method using BCL-xL virus. The virus particles were added to a medium at an MOI of 10, and infection was caused through spin infection (32° C., 900 rpm, centrifugation for 60 minutes). Forced expression of BCL-xL genes was performed by adding DOX to the medium to a concentration of 1 μg/mL.

(1-6) Production and Maintenance Culturing of Megakaryocyte Immortalized Strains 14$^{th}$ to 18$^{th}$ Days of Infection Megakaryocytes self-propagating strains to which the BCL-xL genes were introduced, which were obtained using the method (1-5), were collected, and subjected to centrifugation at 1200 rpm for 5 minutes. After the centrifugation, precipitated cells were suspended in a new differentiation medium, and then disseminated at 2×10⁵ cells/2 mL/well on new C3H10T1/2 feeder cells (6-well plate).

18$^{th}$ Day of Infection: Passage

Megakaryocytes self-propagating strains to which the BCL-xL genes were introduced were collected, the number of cells was counted, and then the cells were disseminated at 3×10⁵ cells/10 mL/100-mm dish.

24$^{th}$ Day of Infection: Passage

Megakaryocytes self-propagating strains to which the BCL-xL genes were introduced were collected, the number of cells was counted, and then the cells were disseminated at 1×10⁵ cells/10 mL/100-mm dish. Subsequently, passage was performed in a similar manner every 4 to 7 days, and maintenance culturing was performed. Note that, in the passage, the cells were suspended in a new differentiation medium, and disseminated.

On the 24$^{th}$ day of infection, megakaryocytes self-propagating strains to which the BCL-xL genes were introduced were collected, immunostained with 2 μL of anti-human CD41a-APC antibody (BioLegend), 1 μL of anti-human CD42b-PE antibody (eBioscience), and 1 μL of anti-human CD235ab-Pacific Blue (Anti-CD235ab-PB; BioLegend) antibody per 1.0×10⁵ cells, and then analyzed using FACS Verse (trademark). Then, on the 24$^{th}$ day of infection, strains with a CD41a positive rate of 50% or more were taken as immortalized megakaryocyte cell lines. The cells that had proliferated for 24 days or more after infection were taken as immortalized megakaryocyte cell lines SeV2-MKCL and NIH5-MKCL.

The obtained SeV2-MKCL and NIH5-MKCL were subjected to stationary culturing using a 10-cm dish (10 mL/dish). The medium was obtained by adding the components listed below to a basal medium IMDM (concentration means final concentration). The culturing conditions were 27° C., 5% $CO_2$.

FBS (sigma #172012 lot.12E261) 15%
L-Glutamin (Gibco #25030-081) 2 mmol/L
ITS (Gibco #41400-045) diluted to 100 times
MTG (monothioglycerol, sigma #M6145-25ML) 450 μmol/L
Ascorbic acid (sigma #A4544) 50 μg/mL
Puromycin (sigma #P8833-100MG) 2 μg/mL
SCF (Wako Pure Chemical Industries, Ltd. #193-15513) 50 ng/mL
TPO-like agonists 200 ng/mL (2) Production of Megakaryocyte Culture The forced expression was canceled by performing culturing in a medium not containing DOX. Specifically, the immortalized megakaryocyte cell lines (SeV2-MKCL and NIH5-MKCL) obtained using the method (1) were washed twice with PBS (−), and suspended in a following platelet producing medium. The cell dissemination density was set to 1.0×10⁵ cells/mL.

The platelet producing medium was obtained by adding the components listed below to a basal medium IMDM (concentration means final concentration).

Human plasma 5%
L-Glutamin (Gibco #25030-081) 4 mmol/L
ITS (Gibco #41400-045) diluted to 100 times
MTG (monothioglycerol, sigma #M6145-25ML) 450 μmol/L
Ascorbic acid (sigma #A4544) 50 μg/mL
SCF (Wako Pure Chemical Industries, Ltd. #193-15513) 50 ng/mL
TPO-like agonists 200 ng/mL
ADAM inhibitor 15 μmol/L
GNF351 (Calbiochem #182707) 500 nmol/LY39983 (Chemscene LLC #CS-0096) 500 nmol/L
Urokinase 5 U/mL
Low-molecular-weight heparin (SANOFI, Clexane) 1 U/mL Then, culturing was performed in the presence of the platelet producing medium for 6 days, so that platelets were produced. Accordingly, a megakaryocyte culture was produced.

(3) Manufacture of Purified Platelets

The megakaryocyte culture obtained in (2) was used to produce platelets (was purified) as follows. Note that similar purification was performed twice.

(3-1) Concentration of Megakaryocyte Culture

The megakaryocyte culture obtained in (2) was introduced to a culture bag. Then, the culture bag was connected to a concentration system as shown in FIG. 1. In FIG. 1, washing and preserving solution bags 1 and 2 contains a washing and preserving solution. As the washing and preserving solution, a solution obtained by adding 20% (v/v %) ACD and 2.5% (w/v %) human serum albumin to a Bicanate injection (Bicarbon infusion, manufactured by Otsuka Pharmaceutical Co., Ltd.) and adjusting the pH to 7.2 using NaOH was used. Then, according to Table 1 below, the megakaryocyte culture was concentrated using a hollow fiber membrane (Plasmatic OP, manufactured by Asahi Kasei Medical Co., Ltd.), and an obtained concentrate of the megakaryocyte culture was collected in a storage bag.

TABLE 1

| Procedure | Open valve | Pump 1 (rpm) | Pump 2 (rpm) | Content |
|---|---|---|---|---|
| 1 | 2, 3, 4 | — | — | 50 mL of washing and preserving solution is introduced from washing and preserving solution bag 1. |
| 2 | 1, 3, 4 | — | — | 50 mL of washing and preserving solution is introduced from washing and preserving solution bag 1. |
| 3 | 5, 6 | — | 100 | 500 mL of washing and preserving solution is introduced from washing and preserving solution bag 2. Pump 2 is operated for 1 minute. |
| 4 | 4, 7 | 50 | — | 500 mL of washing and preserving solution is introduced from washing and preserving solution bag 1. Pump 1 is operated for 1 minute. |
| 5 | 1, 3, 6, 8 | 100 | 100 | Culture is introduced to hollow fiber membrane. |
| 6 | 2, 3, 6, 8 | 100 | 100 | Concentrate is introduced to storage bag. |
| 7 | 2, 3, 4 | — | — | 50 mL of washing and preserving solution is introduced from washing and preserving solution bag 1. |
| 8 | 4, 8 | 50 | — | 500 mL of washing and preserving solution is introduced from washing and preserving solution bag 1. |

(3-2) Centrifugation of Platelets

First, a waste fluid bag of an ACP215 disposable set was replaced with a collecting bag using a sterile tubing welder. As the collecting bag, a Hicaliq IVH bag (Terumo Corporation HC-B3006A) was used. Next, 10% amount of ACD-A solution (manufactured by Terumo Corporation) was added to a concentrate of the megakaryocyte culture. After the addition, a concentrate to which the ACD-A solution had been added was poured into a cell bag. As the cell bag, a Hicaliq IVH bag (HC-B3006A manufactured by Terumo Corporation) was used.

Next, the cell bag containing the culture to which the ACD-A solution had been added was welded to an ACP215 disposable set, using a sterile tubing welder. Then, ACP215 was started up in a service mode, and the number of rotations was set to 2500 rpm (350×g). The ACP215 was started and the culture in the cell bag was introduced to a separator bowl at about 100 mL/min. Liquid components that flowed out from the separator bowl were collected in the collecting bag. After the entire culture in the cell bag was introduced to the separator bowl, 500 mL of washing and preserving solution was introduced to the separator bowl. After the washing and preserving solution was introduced to the separator bowl, the centrifugation was stopped and the collecting bag containing the collected fluid (collected liquid components containing platelets) using a tube sealer.

The collecting bag containing the collected fluid (containing platelets) was welded to a new ACP215 disposable set using the sterile tubing welder. The ACP215 was started up in a normal mode. The program was set to WPC, and the ACP215 disposable set to which the collecting bag had been welded was set according to the device instructions. Note that the collecting bag containing the collected fluid was arranged on a stand.

Next, the centrifugation speed of the ACP215 was changed to 5000 rpm (1398.8×g), and centrifugation was started. When introduction of the collected fluid to the separator bowl was started, the mode was changed from automatic pouring to manual pouring. Specifically, the collected fluid was introduced to the separator bowl at an introduction speed of about 100 mL/min. After the entire collected fluid was added to the separator bowl, 500 mL of washing and preserving solution was further added.

(3-3) Washing of Platelets

According to the program of ACP215, washing was performed using 2000 mL of the washing and preserving solution.

(3-4) Collection of Platelets

According to the program of ACP21, 200 mL of washed platelets was collected in a platelet product bag.

(3-5) Separation of Platelets

Platelets were separated from the platelet product bag using the hollow fiber membrane according to a common method, and collected in the collecting bag (Examples 1-1 to 1-2).

(3-6) Production (Purification) of Platelets of Comparative Examples

As methods for producing platelets of comparative examples, after platelets were separated through filtering from the megakaryocyte culture, the platelets were concentrated using a hollow fiber membrane, and the platelets were washed using the hollow fiber membrane, so that platelets were produced. Four different types of commercially available products were used as filters and hollow fiber membranes (Comparative Examples 1-1 to 1-4).

(4) Measurement of Platelet Collecting Rate, Megakaryocyte Removing Rate, and Platelet Damage The platelet collecting rate, the megakaryocyte removing rate, and the Annexin V positive rate in platelets of the megakaryocyte culture, and the purified platelets obtained using the methods for producing platelets of the examples or the comparative examples were measured using a flow cytometer. Specifically, in measurement of the platelet collecting rate and the megakaryocyte removing rate, 900 μL of diluent was added to a 1.5-mL microtube, 100 μL of megakaryocyte culture or collected material (purified platelets) after platelet purification was added, and the resultant was mixed. Then, 200 μL of obtained solution was poured into a FACS tube, stained by adding the labeled antibody shown below, and analyzed using the flow cytometer. Furthermore, in measurement of the Annexin V positive rate in platelets, 100 μL of megakaryocyte culture and collected material of purified platelets was poured into a FACS tube, and the solution was stained by adding the labeled antibody and proteins shown below, diluted to 5 times with an Annexin V binding buffer (BD Biosciences) immediately before flow cytometer analysis, and then subjected to analysis.

Measurement of platelet collecting rate and megakaryocyte removing rate
- 1.0 μL anti-CD41a antibody APC label (Bio Legend 303710)
- 1.0 μL anti-CD42a antibody PB label (eBioscience 48-0428-42)
- 1.0 μL anti-CD42b antibody PE label (Bio Legend 303906)

Measurement of platelet damage
- 1.0 μL anti-CD41a antibody APC label (Bio Legend 303710)
- 1.0 μL anti-CD42b antibody PE label (Bio Legend 303906)
- 5 μL Annexin V FITC label (BD Biosciences 556419)

(4-1) Platelet Collecting Rate and Megakaryocyte Removing Rate

Platelets and megakaryocytes were divided from each other according to the particle size indicated by forward scatter (FSC) and side scatter (SSC), and, in each division, particles that were positive for CD41a and CD42b were taken as platelets, and particles that were positive for CD41a, CD42a, and CD42b were taken as megakaryocytes, and thus the number of platelets and the number of megakaryocytes in the megakaryocyte culture and the purified platelets were calculated. Then, the platelet collecting rate and the megakaryocyte removing rate were calculated based on the obtained number of platelets and number of megakaryocytes. The platelet collecting rate was calculated according to Equation (3) below, and the megakaryocyte removing rate was calculated according to Equation (4) below. Table 2 below shows the results.

$$C = P_a / P_b \quad (3)$$

C: Platelet collecting rate (%)
$P_b$: Number of platelets in megakaryocyte culture
$P_a$: Number of platelets in purified platelets $$R = (Mb - Ma) / Mb \quad (4)$$

R: Megakaryocyte removing rate (%)
Mb: Number of megakaryocytes in megakaryocyte culture
Ma: Number of megakaryocytes in purified platelets

TABLE 2

|  | Platelet collecting rate (%) | Megakaryocyte removing rate (%) |
|---|---|---|
| Example 1-1 | 60.1 | 100.0 |
| Example 1-2 | 78.6 | 99.4 |
| Comparative Example 1-1 | 50.9 | 95.3 |
| Comparative Example 1-2 | 2.1 | 100.0 |
| Comparative Example 1-3 | 41.9 | 92.8 |
| Comparative Example 1-4 | 14.3 | 99.8 |

As shown in Table 2 above, Examples 1-1 and 1-2 exhibited megakaryocyte removing rates greater than or equal to those of Comparative Examples 1-1 to 1-4, and it is seen that platelets can be purified to a sufficient purity according to the examples. Furthermore, it is seen that Examples 1-1 and 1-2 had platelet collecting rates greater than those of Comparative Examples 1-1 to 1-4.

(4-2) Platelet Damage

The percentage of Annexin V positive particles with respect to the CD41a and CD42b positive and CD42a negative particles was measured. The variation was calculated by subtracting the percentage of Annexin V positive particles with respect to the megakaryocyte culture from the percentage of Annexin V positive particles with respect to the purified platelets.
Table 3 below shows the results.

TABLE 3

|  | Annexin V positive in megakaryocyte culture (%) | Annexin V positive in purified platelets (%) | Variation (%) |
|---|---|---|---|
| Example 1-1 | 14.1 | 12.7 | -1.4 |
| Example 1-2 | 11.5 | 9.3 | -2.2 |
| Comparative Example 1-1 | 12.2 | 14.4 | 2.2 |
| Comparative Example 1-2 | 12.2 | 24.9 | 12.7 |
| Comparative Example 1-3 | 12.2 | 17.3 | 5.1 |
| Comparative Example 1-4 | 12.2 | 27.9 | 15.7 |

As shown in Table 3 above, the percentage of Annexin V positive particle increased in Comparative Examples 1-1 to 1-4, meaning that platelets were damaged. On the other hand, the percentage of Annexin V positive particles decreased in Examples 1-1 and 1-2, meaning that platelets were not damaged.

It is seen from the description above that, according to the method for producing platelets of the present invention, damage to platelets is suppressed compared with the above-described method. Furthermore, it is seen that, according to the method for producing platelets of the present invention, the efficiency in collecting platelets is improved compared with the above-described method.

Example 2

It was checked whether or not, according to the method for producing platelets of the present invention, purified platelets can be produced in a shorter period of time compared with the time that is taken to perform the above-described method so as to reduce damage to platelets.

The treatment time necessary to produce platelets from 50000 mL of the megakaryocyte culture as in Example 1 (3) above according to a method for producing platelets of Example and a method for producing platelets of Comparative Example was simulated. Note that the introduction speeds (treatment speeds) in the steps were set to those at which damage to platelets is reduced when the treatment steps are actually performed. Note that, in washing, 3000 mL of washing and preserving solution was added. Tables 4A and 4B below show the results.

TABLE 4A

| Example | Concentration (Concentration with hollow fiber membrane) | Centrifugation (Separation with ACP) | Washing (Washing with ACP) | Separation of Platelets (Separation with filter) | Total treatment time (min) |
|---|---|---|---|---|---|
| Input fluid amount (mL) | 50000 | 2500 | 2800 + 3000 | 250 | — |
| Output fluid amount (mL) | 2500 | 2800 | 250 | 250 | — |
| Treatment speed (mL/min) | 300 | 200 | 100 | 20 | — |
| Treatment time (min) | 158 | 12.5 | 58 | 12.5 | 241 |

TABLE 4B

| Comparative Example | Separation with filter | Concentration with hollow fiber membrane | Washing with hollow fiber membrane | Total treatment time (min) |
|---|---|---|---|---|
| Input fluid amount (mL) | 50000 | 50000 | 2500 | — |
| Output fluid amount (mL) | 50000 | 2,500 | 250 | — |
| Treatment speed (mL/min) | 200 | 300 | 100 | — |
| Treatment time (min) | 250 | 167 | 45 | 462 |

As shown in Tables 4A and 4B above, the total treatment time according to the method for producing platelets of Comparative Example was 462 minutes, whereas the total treatment time according to the method for producing platelets of the present invention was 241 minutes, meaning that the treatment time was shortened by half.

It is seen from the description above that, according to the method for producing platelets of the present invention, purified platelets can be produced in a shorter period of time compared with the time that is taken to perform the above-described method so as to reduce damage to platelets.

Example 3

It was checked whether or not, according to the preserving solution of the present invention, a deterioration in platelets during preservation can be suppressed.

Platelets were purified in a similar way to that of Example 1 above, except that washed platelets were collected using a preserving solution. The preserving solution used was obtained by adding a 5 v/v % ACD-A solution (ACD-A solution 5 mL per L of Bicanate injection) and human serum albumin to a predetermined concentration (0, 1.25 or 5 w/v %), to a Bicanate injection, and adjusting the pH to 7.2 using NaOH. Table 5 below shows the compositions of the preserving solutions.

TABLE 5

| | Albumin concentration | | |
|---|---|---|---|
| | 0% | 1.25% | 5% |
| Potassium chloride (w/v %) | 0.0286 | 0.0286 | 0.0286 |
| Calcium chloride hydrate (w/v %) | 0.0210 | 0.0210 | 0.0210 |
| Magnesium chloride (w/v %) | 0.0190 | 0.0190 | 0.0190 |
| Sodium hydrogen carbonate (w/v %) | 0.2238 | 0.2238 | 0.2238 |
| Sodium citrate hydrate (w/v %) | 0.1238 | 0.1238 | 0.1238 |
| Citric acid hydrate (w/v %) | 0.0381 | 0.0381 | 0.0381 |

TABLE 5-continued

| | Albumin concentration | | |
|---|---|---|---|
| | 0% | 1.25% | 5% |
| Dextrose (w/v %) | 0.1048 | 0.1048 | 0.1048 |
| Human serum albumin (w/v %) | 0.0000 | 1.2500 | 5.0000 |

Next, platelets in the preserving solution were preserved at 22° C. for 24, 48, 72, or 168 hours. The preservation temperature was set to 22° C., and the platelets were agitated by gently shaking a bag containing the platelets during preservation. Then, platelets at the start of preservation (0 hours) and platelets after preservation were collected, and the percentages of Annexin V positive particles were measured in a similar way to that of Example 1 (4) above. Table 6 below shows the results. In Table 6 below, the percentage shown in a parenthesis means the percentage of Annexin V positive particles increased with respect to the particles at the start of preservation.

TABLE 6

| | 0 Hours | 24 Hours | 48 Hours | 72 Hours | 168 Hours |
|---|---|---|---|---|---|
| 0% Human serum albumin | 10.2% | 14.5% (+4.3%) | 15.1% (+4.9%) | 19.2% (+9.0%) | 46% (+35.8%) |
| 1.25% Human serum albumin | 7.3% | — | — | 14.0% (+6.7%) | 19.6% (+12.3%) |
| 5% Human serum albumin | 7.3% | 9.0% (+1.7%) | 10.0% (+2.7%) | 13.3% (+6.0%) | — |

—: Not tested

As shown in Table 6 above, compared with the platelets preserved in the preserving solution to which human serum albumin was not added, the percentage of Annexin V positive particles with respect to the platelets preserved in the preserving solutions to which human serum albumin was added decreased, that is, the percentage of damaged platelets decreased, in all points in time after preservation. Furthermore, when the concentration of the human serum albumin was increased, the percentage of damaged platelets decreased. Moreover, compared with the platelets preserved in the preserving solution to which human serum albumin was not added, an increase in Annexin V positive particles in the platelets preserved in the preserving solutions to which human serum albumin was added was significantly suppressed 168 hours after preservation.

It is seen from the description above that, according to the preserving solution of the present invention, a deterioration in platelets during preservation can be suppressed, and, in particular, this preserving solution can be preferably used for long-term preservation of platelets.

Example 4

It was checked whether or not, according to the preserving solution of the present invention, damage to platelets during centrifugation can be suppressed.

(1) Preparation of Washing and Preserving Solution

The washing and preserving solution used in the first centrifuging step and the second centrifuging step was obtained by adding 2.5 w/v % human serum albumin, and an ACD-A solution to a predetermined concentration (5, 10, or 20v/v %), to a Bicanate injection, and adjusting the pH to 7.2 using NaOH. Table 7 below shows the compositions of the preserving solutions.

TABLE 7

|  | 5% ACD-A | 10% ACD-A | 20% ACD-A |
| --- | --- | --- | --- |
| Potassium chloride (w/v %) | 0.0286 | 0.0273 | 0.0250 |
| Calcium chloride hydrate (w/v %) | 0.0210 | 0.0200 | 0.0183 |
| Magnesium chloride (w/v %) | 0.0190 | 0.0182 | 0.0167 |
| Sodium hydrogen carbonate (w/v %) | 0.2238 | 0.2136 | 0.1958 |
| Sodium citrate hydrate (w/v %) | 0.1238 | 0.2182 | 0.3833 |
| Citric acid hydrate (w/v %) | 0.0381 | 0.0727 | 0.1333 |
| Dextrose (w/v %) | 0.1048 | 0.2000 | 0.3667 |
| Human serum albumin (w/v %) | 2.5000 | 2.5000 | 2.5000 |

(2) Damage to Platelets

Next, platelets were centrifuged in a similar way to that of Example 1 (3-2) above, except that the washing and preserving solution prepared in Example 4 (1) above was used as the washing and preserving solution. Platelets were collected before centrifugation, after the first centrifugation (centrifugation at 350×g), and after the second centrifugation (centrifugation at 1398.8×g), and the percentages of Annexin V positive particles were measured in a similar way to that of Example 1 (4) above. Table 8 below shows the results.

TABLE 8

|  | Before centrifugation | After first centrifugation | After second centrifugation |
| --- | --- | --- | --- |
| 0% ACD-A | 30% | — | — |
| 5% ACD-A | 26% | 32% (+6%) | 37% (+11%) |
| 10% ACD-A | 21% | 26% (+5%) | 30% (+9%) |

TABLE 8-continued

|  | Before centrifugation | After first centrifugation | After second centrifugation |
| --- | --- | --- | --- |
| 20% ACD-A | 13% | 14% (+1%) | 18% (+5%) |

—: Not tested

As shown in Table 8 above, damage to platelets during centrifugation decreased in accordance with an increase in the amount of ACD-A solution added. Furthermore, the concentrations of the electrolyte and the sugar in the washing and preserving solutions were as shown in Table 7, and satisfy the numeric range of the concentrations of the electrolyte and the sugar shown in the embodiments. Therefore, it is seen that within the numeric range of the concentrations of the electrolyte and the sugar shown in the embodiments, damage to platelets during centrifugation can be suppressed.

It is seen from the description above that, according to the preserving solution of the present invention, damage to platelets during centrifugation can be suppressed.

While the present invention has been described above with reference to illustrative example embodiments, the present invention is by no means limited thereto. Various changes and variations that may become apparent to those skilled in the art may be made in the configuration and specifics of the present invention without departing from the scope of the present invention.

This application claims priority from Japanese Patent Application No. 2017-179138 filed on Sep. 19, 2017. The entire subject matter of the Japanese Patent Application is incorporated herein by reference.

(Supplementary Notes)

Some or all of the above embodiments and examples may be described as in the following Supplementary Notes, but are not limited thereto.

(Supplementary Note 1)

A method for producing purified platelets, including:
  a concentrating step of concentrating a megakaryocyte culture; and
  a centrifuging step of centrifuging platelets from an obtained concentrate.

(Supplementary Note 2)

The method for producing purified platelets according to Supplementary Note 1, wherein the centrifuging step includes:
  a first centrifuging step of separating the concentrate at a centrifugal force of 150 to 550 g; and
  a second centrifuging step of centrifuging liquid components collected in the first centrifuging step at a centrifugal force of 600 to 4000 g.

(Supplementary Note 3)

The method for producing purified platelets according to Supplementary Note 2, wherein the centrifuging step is performed using a centrifugal separator including:
  a rotatable separator bowl having an inner wall to which a component with a large specific gravity in the concentrate or the collected liquid components is attached according to a centrifugal force, and an outlet port through which liquid components after separation of the concentrate or the collected liquid components flow out according to the centrifugal force; and
  a collecting unit for collecting the liquid components that have flowed out from the outlet port.

(Supplementary Note 4)
The method for producing purified platelets according to Supplementary Note 3, further including:
  a washing step of, after the second centrifuging step, performing washing by adding a washing and preserving solution to the separator bowl and rotating the separator bowl; and
  a platelet collecting step of, after the washing step, collecting platelets by swinging the separator bowl containing the washing and preserving solution and introducing air from the outlet port of the separator bowl.

(Supplementary Note 5)
The method for producing purified platelets according to Supplementary Note 4, further including:
  a separated component collecting step of, before the washing step, collecting separated components in the separator bowl after the second centrifuging step; and
  a separated component concentrating step of concentrating the separated components,
    wherein, in the washing step, washing is performed by adding concentrated separated components and a washing and preserving solution to the separator bowl and rotating the separator bowl.

(Supplementary Note 6)
The method for producing purified platelets according to Supplementary Note 4 or 5, further including a platelet separating step of separating the collected platelets, by causing the platelets to pass through a separating member.

(Supplementary Note 7)
The method for producing purified platelets according to Supplementary Note 6, wherein, in the platelet separating step, the collected platelets are introduced to the separating member by causing the platelets to naturally fall.

(Supplementary Note 8)
The method for producing purified platelets according to any one of Supplementary Notes 1 to 7, wherein the concentrating step is performed using a concentrating member.

(Supplementary Note 9)
The method for producing purified platelets according to Supplementary Note 5, wherein the separated component concentrating step is performed using a concentrating member.

(Supplementary Note 10)
The method for producing purified platelets according to any one of Supplementary Notes 1 to 9, further including a producing step of, before the concentrating step, producing a megakaryocyte culture,
  wherein the producing step includes:
    a first expressing step of forcibly expressing an oncogene and a polycomb gene in cells that are more undifferentiated than megakaryocytes; and
    a second expressing step of forcibly expressing Bcl-xL genes in the undifferentiated cells; and
    a canceling step of canceling all of the forced expression.

(Supplementary Note 11)
A method for producing a platelet product, including a product producing step of producing a platelet product from purified platelets,
  wherein the purified platelets are obtained using the method for producing purified platelets according to any one of Supplementary Notes 1 to 10.

(Supplementary Note 12)
A method for producing a blood product, including a blood product producing step of producing a blood product by mixing purified platelets and other components,
  wherein the purified platelets are obtained using the method for producing purified platelets according to any one of Supplementary Notes 1 to 10.

(Supplementary Note 13)
A platelet preserving solution including albumin.

(Supplementary Note 14)
The platelet preserving solution according to Supplementary Note 13, wherein a concentration of the albumin is 1.25 w/v % or more.

(Supplementary Note 15)
The platelet preserving solution according to Supplementary Note 14, wherein a concentration of the albumin is 10 w/v % or less.

(Supplementary Note 16)
The platelet preserving solution according to any one of Supplementary Notes 13 to 15, wherein the albumin is serum albumin.

(Supplementary Note 17)
The platelet preserving solution according to any one of Supplementary Notes 13 to 16, further including a sugar.

(Supplementary Note 18)
The platelet preserving solution according to Supplementary Note 17, wherein a concentration of the sugar is 0.1 to 0.4 w/v %.

(Supplementary Note 19)
The platelet preserving solution according to Supplementary Note 17 or 18, wherein the sugar is dextrose.

(Supplementary Note 20)
The platelet preserving solution according to any one of Supplementary Notes 13 to 19, further including an electrolyte.

(Supplementary Note 21)
The platelet preserving solution according to Supplementary Note 20, wherein the electrolyte includes at least one selected from the group consisting of sodium chloride, potassium chloride, calcium chloride, magnesium chloride, sodium hydrogen carbonate, sodium citrate, and citric acid.

(Supplementary Note 22)
A platelet preserving agent including albumin.

(Supplementary Note 23)
The platelet preserving agent according to Supplementary Note 22, wherein the albumin is serum albumin.

(Supplementary Note 24)
The platelet preserving agent according to Supplementary Note 22 or 23, further including a sugar.

(Supplementary Note 25)
The platelet preserving agent according to Supplementary Note 24, wherein the sugar is dextrose.

(Supplementary Note 26)
The platelet preserving agent according to any one of Supplementary Notes 22 to 25, further including an electrolyte.

(Supplementary Note 27)
The platelet preserving agent according to Supplementary Note 26, wherein the electrolyte includes at least one selected from the group consisting of sodium chloride, potassium chloride, calcium chloride, magnesium chloride, sodium hydrogen carbonate, sodium citrate, and citric acid.

(Supplementary Note 28)
A method for preserving platelets, including a preserving step of preserving platelets in the presence of albumin.

(Supplementary Note 29)
The method for preserving platelets according to Supplementary Note 28, wherein a concentration of the albumin is 1.25 w/v % or more.

(Supplementary Note 30)
30. The method for preserving platelets according to Supplementary Note 29, wherein a concentration of the albumin is 10 w/v % or less.
(Supplementary Note 31)
31. The method for preserving platelets according to any one of Supplementary Notes 28 to 30, wherein the albumin is serum albumin.
(Supplementary Note 32)
32. The method for preserving platelets according to any one of Supplementary Notes 28 to 31, wherein the preserving step is performed in the presence of a sugar.
(Supplementary Note 33)
The method for preserving platelets according to Supplementary Note 32, wherein a concentration of the sugar is 0.1 to 0.4 w/v %.
(Supplementary Note 34)
The method for preserving platelets according to Supplementary Note 32 or 33, wherein the sugar is dextrose.
(Supplementary Note 35)
The method for preserving platelets according to any one of Supplementary Notes 28 to 34, wherein the preserving step is performed in the presence of an electrolyte.
(Supplementary Note 36)
The method for preserving platelets according to Supplementary Note 35, wherein the electrolyte includes at least one selected from the group consisting of sodium chloride, potassium chloride, calcium chloride, magnesium chloride, sodium hydrogen carbonate, sodium citrate, and citric acid.

INDUSTRIAL APPLICABILITY

As described above, according to the method for producing platelets of the present invention, a megakaryocyte culture is concentrated before platelets are separated. Therefore, according to the method for producing platelets of the present invention, it is possible to reduce the volume of a sample (e.g., a concentrate) subjected to the centrifuging step. Therefore, according to the method for producing platelets of the present invention, the time necessary to separate the platelets in the centrifuging step can be shortened, and the time that is taken to purify platelets from the megakaryocyte culture can be shortened, and thus it is possible to obtain platelets in a shorter period of time compared with the above-described method. Furthermore, according to the producing method of the present invention, when separating platelets, it is not necessary to process a large amount of megakaryocyte culture in separation through filtering, and thus, for example, damage to platelets that may occur when the flow rate is increased in the above-described method can be avoided. Therefore, according to the method for producing platelets of the present invention, damage to platelets is suppressed compared with the above-described method. Therefore, the present invention is extremely useful, for example, in the cellular medicine field and medical field in which platelets are used.

The invention claimed is:

1. A method for producing purified platelets, comprising:
concentrating a solid fraction of a megakaryocyte culture containing megakaryocytes and platelets by passing the megakaryocyte culture through a hollow fiber membrane so as to obtain a concentrate; and
centrifuging platelets from the concentrate,
wherein the centrifuging includes:
separating the concentrate at a centrifugal force of 150 to 550×g and collecting liquid components of the concentrate; and
centrifuging the liquid components of the concentrate at a centrifugal force of 600 to 4000×g.

2. The method for producing purified platelets according to claim 1, further comprising producing the megakaryocyte culture before the concentrating,
wherein the producing includes:
forcibly expressing an oncogene and a polycomb gene in cells that are more undifferentiated than megakaryocytes;
forcibly expressing Bcl-XL genes in cells that are more undifferentiated than megakaryocytes; and
canceling all of the forced expression.

3. A method for producing a platelet product, comprising a product producing step of producing a platelet product from purified platelets,
wherein the purified platelets are obtained using the method for producing purified platelets according to claim 1.

4. A method for producing a blood product, comprising a blood product producing step of producing a blood product by mixing purified platelets and other components,
wherein the purified platelets are obtained using the method for producing purified platelets according to claim 1.

* * * * *